United States Patent
Prager et al.

(10) Patent No.: US 8,062,225 B1
(45) Date of Patent: *Nov. 22, 2011

(54) IMMERSION BAG SYSTEM FOR USE WITH AN ULTRASOUND PROBE

(75) Inventors: Thomas C. Prager, Spicewood, TX (US); Thomas A. Burba, Plymouth, MN (US); David R. Hardten, Orono, MN (US); William T. Ryder, Victoria, MN (US)

(73) Assignee: ESI, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/066,309

(22) Filed: Apr. 12, 2011

Related U.S. Application Data

(63) Continuation-in-part of application No. 11/701,235, filed on Feb. 1, 2007, now Pat. No. 8,012,095, which is a continuation-in-part of application No. 11/356,873, filed on Feb. 17, 2006, now Pat. No. 8,012,094.

(51) Int. Cl.
*A61B 8/14* (2006.01)
(52) U.S. Cl. .................................................. 600/459
(58) Field of Classification Search .................. 600/459
See application file for complete search history.

*Primary Examiner* — Tse Chen
*Assistant Examiner* — Hien Nguyen
(74) *Attorney, Agent, or Firm* — Hugh D. Jaeger

(57) ABSTRACT

An immersion bag system for use with an ultrasound probe to overcome near field artifact including a flexible thin wall thickness immersion bag with an attached flexible collar having an integral internal seal. The immersion bag contains a gel or other ultrasound transmission medium and is sealingly and removably attached by a mutually formed probe/seal valve to the tip end of an ultrasound probe. The immersion bag is able to conform to a cornea, as well as to other surfaces, whether flat or irregular, thereby enabling an ultrasound probe to be used easily on such surfaces. An ultrasound probe, in use with the immersion bag system, is maintained at a distance above the contact surface of the immersion bag and is positionable about the vertical axis while the immersion bag maintains stationary conformal contact with the structure against which it is in contact.

42 Claims, 29 Drawing Sheets

IMMERSION BAG SYSTEM FOR USE WITH AN ULTRASOUND PROBE

CROSS REFERENCES TO RELATED APPLICATIONS

This patent application is a continuation-in-part (CIP) of application Ser. No. 11/701,235 entitled "Immersion Bag System for Use With an Ultrasound Probe" filed Feb. 1, 2007, now U.S. Pat. No. 8,012,095, which is a continuation-in-part (CIP) of application Ser. No. 11/356,873 entitled "Immersion Bag System for Use With an Ultrasound Probe" filed Feb. 17, 2006, now U.S. Pat. No. 8,012,094, and is hereby incorporated into this application by reference as if fully set forth herein.

BACKGROUND OF THE INVENTION

1. Field of the Invention

The present invention primarily applies to the medical device field, and more particularly, pertains to an immersion bag system having an immersion bag of acoustically invisible material and a flexible sealing collar which when engaged with a body of an ultrasound probe forms a deformable valve which can also serve as a pressure release valve. The bag encapsulates the distal end of and is incorporated into use with an ultrasound probe. The immersion bag system, suitable for containment of a gel or other aqueous medium of any suitable viscosity, overcomes near field artifact allowing the examination of shallow anatomical structures. In operation of the invention the distal end of the ultrasound probe, including a transducer, is immersed in the gel or other aqueous medium.

Definition of "near field artifact". Typically, a stationary ultrasound probe passes or scans over just 10 degrees during ultrasound scanning, but by physically moving the ultrasound probe transducer head back and forth via a motor or other suitable means, a range of 120 degrees can be examined. However, when the ultrasound probe transducer head moves, the consequential pulsating of the ultrasound waves collide with one another creating interference which results in an acoustic dead zone. Structures contained within this dead zone cannot be visualized and this is termed "near field artifact". Therefore, examining shallow/superficial tissue with a moving ultrasound probe, anatomical structures within the near field artifact cannot be visualized because of the near field artifact and requires standoff or physical separation between the end of the ultrasound probe and the anatomical structure.

This invention has medical and industrial applications by enhancing the ability to exam shallow/superficial structures amenable to ultrasound evaluation. Medical and industrial sonogram examinations may be improved by this method of overcoming near field artifact (defined previously). This includes:

a. anterior ocular structures, e.g., the cornea, iris, iris angle, lens, ciliary body, as well as structures on the side of the eye;

b. skin lesions, e.g., skin cancers, cysts, or neoplasms;

c. vascular structure/flow assessment; and, d. industrial monitoring of flow characteristics in tubing.

2. Description of the Prior Art

Ultrasound scans of the eye or other areas of the body are performed using an ultrasound probe and a coupling medium placed between the ultrasound probe tip and the surface of the area being scanned during examination to overcome near field artifact. The medium, such as a gel or other less viscous aqueous medium, allows for the transmission of ultrasound waves between the ultrasound probe and through human tissue or other structures. To eliminate the near field artifact, the ultrasound probe tip and the superficial structures under examination, such as blood vessels or anterior aspects of the eye, must be separated at a distance from each other and not in direct contact. A common method of accomplishing this is to use a cylindrical shaped cup that is open on both ends which can contain gel or other suitable aqueous medium and which is placed over the area of the examining surface. The use of an open cylindrical shaped cup requires that the operator fill the cup with gel or other suitable aqueous medium. An excessive filling of the cup may result in undesirable overrun of the cup when the tip of the ultrasound probe is introduced therein and the coupling gel, e.g., methylcellulose, may be an eye irritant. An insufficient filling of the cup results in less than desirable ultrasound scan examination because the near field artifact opaque zone cannot be overcome, thus preventing an examination of the structure under study. If a cylinder with an open bottom, i.e., a cup, is used, the gel or other suitable aqueous medium must be at a depth to allow a sufficient probe distance from the exam surface to overcome the opaque zone created by the near field artifact. More importantly, the shell of hard plastic or thick silicone can readily come into contact with the delicate cornea causing an abrasion. The acoustically transparent immersion bag of the present invention eliminates the need for tedious and correct medium filling to a proper level and provides for ultrasound probe separation from the exam surface to overcome the near field artifact, thereby allowing visualization of superficial structures of the body and/or other structures during the ultrasound exam. Further, with the open cylinder technique, the ultrasound probe may readily come into contact with the sensitive cornea of the eye. Transmission of microorganisms is possible with the open cylinder technique as sterilization of the ultrasound probe and open shell is difficult and time consuming.

SUMMARY OF THE INVENTION

The general purpose of the present invention is the creation of an immersion bag system, portions of which are fabricated from acoustically invisible material such as polyethylene, hydrophilic plastic or other suitable thin flexible material which encapsulate the tip of an ultrasound probe. The immersion bag, suitable for containment of a gel or other aqueous medium, overcomes near field artifact thereby allowing the examination of shallow/superficial structures. The immersion bag is permanently attached to a flexible collar which seals around the distal end of the closely associated ultrasound probe outer case. When the ultrasound probe is inserted into the immersion bag, the immersion bag becomes a cylindrical or other shaped bag with positive internal pressure. During an examination, this internal positive pressure in the immersion bag inhibits the ultrasound probe from moving forward and contacting nearby structures, such as the cornea of the eye. Also, the ultrasound probe is encapsulated by the sterile immersion bag, thus reducing the likelihood of transmission of microorganisms from patient-to-patient.

According to one or more embodiments of the present invention, there is an immersion bag system having a flexible compressible collar and an immersion bag attached thereto which is collectively used to encapsulate the tip portion of an ultrasound probe. The immersion bag system, which can contain preloaded or site loaded gel or other suitable aqueous medium, engages and surrounds the distal end of the ultrasound probe to an adequate depth to overcome the near field artifact. The mutually secured immersion bag and flexible collar are comprised of flexible and pliable materials. Specifically, the flexible collar includes an open end for inserting the ultrasound probe and also includes an integral flexible seal. The acoustically invisible immersion bag is attached to the flexible collar, each having annular qualities. A lip of the immersion bag is permanently secured within the flexible collar by a rigid or semi-rigid capture ring or by other suitable attachment methods. Additionally, the flexible seal, which is integral to the flexible collar, frictionally engages the body of the ultrasound probe upon introduction therein to form a deformable probe/seal valve therebetween which is watertight. By inserting the ultrasound probe into the partially liquid filled immersion bag, slight hydraulic (internal) pressure is created effectively eliminating bag material wrinkles, which is a source of acoustical artifact, thereby forming and ensuring a smooth surface shape of the immersion bag. A consequence of positive internal hydraulic pressure is the resistance created on the ultrasound probe when moved into the immersion bag, thereby minimizing the possibility of physical contact by the ultrasound probe with the superficial structures under examination, such as the sensitive cornea of the eye. Canting or otherwise reorienting of the ultrasound probe with respect to the flexible seal and flexible collar can deformingly open the probe/seal valve to lower internal bag air pressure or can release excess gel or aqueous medium from the immersion bag. To maintain immersion bag shape and integrity, venting can be provided by one or more self-sealing valves to release air, excess gel, or other excess aqueous medium from the immersion bag during insertion of the ultrasound probe or during operation of the invention in order to maintain optimum positive internal immersion bag pressure. The internal pressure of the bag must be lower than the pressure of the eye or the cornea will dent. By using the seal to release air/fill and regulating the amount of bag fill, an eye with low pressure can be examined. The internal pressure and bag tension also provides resistance and tactile feedback to the operator when moving the ultrasound probe toward the immersion bag end. This internal immersion bag pressure and bag tension offsets the ultrasound probe tip from the examined surface, thus overcoming near field artifact, and due to resistance, maintains spacing between the transducer and the immersion bag end. The end of the immersion bag is conformally reshaped to mirror and envelop the examining surface upon contact. Moreover, being flexible and pliable, the immersion bag conforms to irregularly shaped anatomical areas, such as, but not limited to, the cornea, nose region or eyelid.

The flexible immersion bag accommodates off-center and angular positioning of the ultrasound probe for off-center ultrasound scans such as a lesion on the side of the eye (sclera). Thus, while the immersion bag is immobile, the ultrasound probe can be angled within the immersion bag. The immersion bag end also can be rolled on the examined surface for acquiring angled ultrasound images at various angles while still maintaining a spaced relationship with the examined surface. This minimizes potential damage to sensitive and delicate tissues such as the cornea. The ultrasound probe and immersion bag containing the liquid medium can easily be moved and repositioned on different anatomical areas to be examined without consequence to the cornea.

One significant aspect and feature of the present invention is a sterile acoustically invisible immersion bag of an immersion bag system that fully encapsulates one end of an ultrasound probe.

Another significant aspect and feature of the present invention includes an acoustically invisible immersion bag system where a flexible collar including a flexible seal and a rigid or semi-rigid capture ring in cooperation with an immersion bag surrounds and engages the distal end portion of the ultrasound probe.

Still another significant aspect and feature of the present invention is the flexible collar and closely associated structure which effectively secures and seals to the ultrasound probe body to form a probe/seal valve which is deformable.

Still another significant aspect and feature of the present invention is the use of internal immersion bag pressure to enhance the intimate engagement of a flexible seal to the ultrasound probe.

Still another significant aspect and feature of the present invention is an immersion bag system which can be preloaded or loaded on site with a gel or other aqueous medium.

Yet another significant aspect and feature of the present invention is an immersion bag wherein gel or other aqueous medium is contained and encapsulated about and between the distal end of an ultrasound probe and the interior of the immersion bag.

Another significant aspect and feature of the present invention is a flexible collar which can include controlled pressure venting for air, gases, gels or other aqueous medium.

Yet another significant aspect and feature of the present invention is where a flexible immersion bag accommodates off-center positioning of the ultrasound probe for off-center ultrasound scans; hence, the immersion bag is stationary and the ultrasound probe moves within the immersion bag or can be rolled on the examined area and achieve similar results so there is no or minimal abrasive contact with delicate or sensitive structures.

Another significant aspect and feature of the present invention is an immersion bag including a flexible collar that functions in cooperation with the body of an ultrasound probe to form a self-sealing valve which can by itself or in combination with additional valves with the flexible collar provide passive control of the internal pressure in the immersion bag during ultrasound probe insertion, thereby allowing the examination of eyes with low pressure.

Another significant aspect and feature of the present invention is the utilization of internal immersion bag hydraulic pressure and bag material tension creating buoyancy and resistance on the ultrasound probe when the operator is moving the ultrasound probe deeper into the immersion bag into close proximity with the examined surface. Further, once the ultrasound probe has been inserted into the immersion bag, the consequential positive hydraulic pressure is a safety feature minimizing the likelihood of the ultrasound probe making physical contact with nearby superficial structures such as the cornea of the eye. Thus, there is an offset of the ultrasound probe from the examined surface that overcomes near field artifact.

Another significant aspect and feature of the present invention is the use of a maneuvering ring which surrounds a flexible collar and other closely associated components to provide a measured amount of rigidity in order that the user can grasp and position the immersion bag with respect to the eye.

Another significant aspect and feature of the present invention is the use of a maneuvering ring having an interior annular receptor groove which engages, couples and mates with an exterior annular ring of the flexible collar for mutual joining thereof in order to fasteningly accommodate the lip of the immersion bag and other closely associated components.

Another significant aspect and feature of the present invention is the use of an O-ring or band to depress a portion of the immersion bag lip into an annular interior groove of a capture ring to secure the immersion bag to the capture ring.

Yet another significant aspect and feature of the present invention is the use of an immersion bag substantially having a conical shape for the greatest portion thereof which includes an end which is arcuate in profile, whereby such an arcuate end reversibly conforms to the shape of the cornea.

Yet another significant aspect and feature of the present invention is that examination of ocular structures does not require coupling gel on the bag outer surface.

Another embodiment of the present invention includes additional aspects and features wherein:

Another significant aspect and feature of the present invention is the use of a semi rigid flexible collar having a flexible seal which includes an annular sealing edge which sealingly aligns to the ultrasound probe body section to form a probe/seal valve.

Another significant aspect and feature of the present invention is the use of a semi rigid flexible collar having an internal capture annulus.

Another significant aspect and feature of the present invention is the use of a capture ring of heavy cardboard or paper.

Another significant aspect and feature of the present invention is the use of a flexible seal which engages, couples and mates with an internal capture annulus of the flexible collar for mutual joining thereof in order to fasteningly accommodate the lip of the immersion bag and other closely associated components.

Another significant aspect and feature of the present invention is the use of a probe/seal valve which is manually deformable to form temporary gaps between the annular sealing edge and the nontapered ultrasound probe body section to vent the interior of the immersion bag for the removal of air or liquid therefrom.

Having thus briefly described one or more embodiments of the present invention and having mentioned some significant aspects and features of the present invention, it is the principal object of the present invention to provide a acoustically invisible immersion bag system that overcomes near field artifact by surrounding the tip portion of an ultrasound probe tip with gel or liquid contained in an immersion bag removably secured by the use of a probe/seal valve to and about an ultrasound probe via a flexible collar that may contain self-sealing valve structure for venting excess air or excess liquid.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
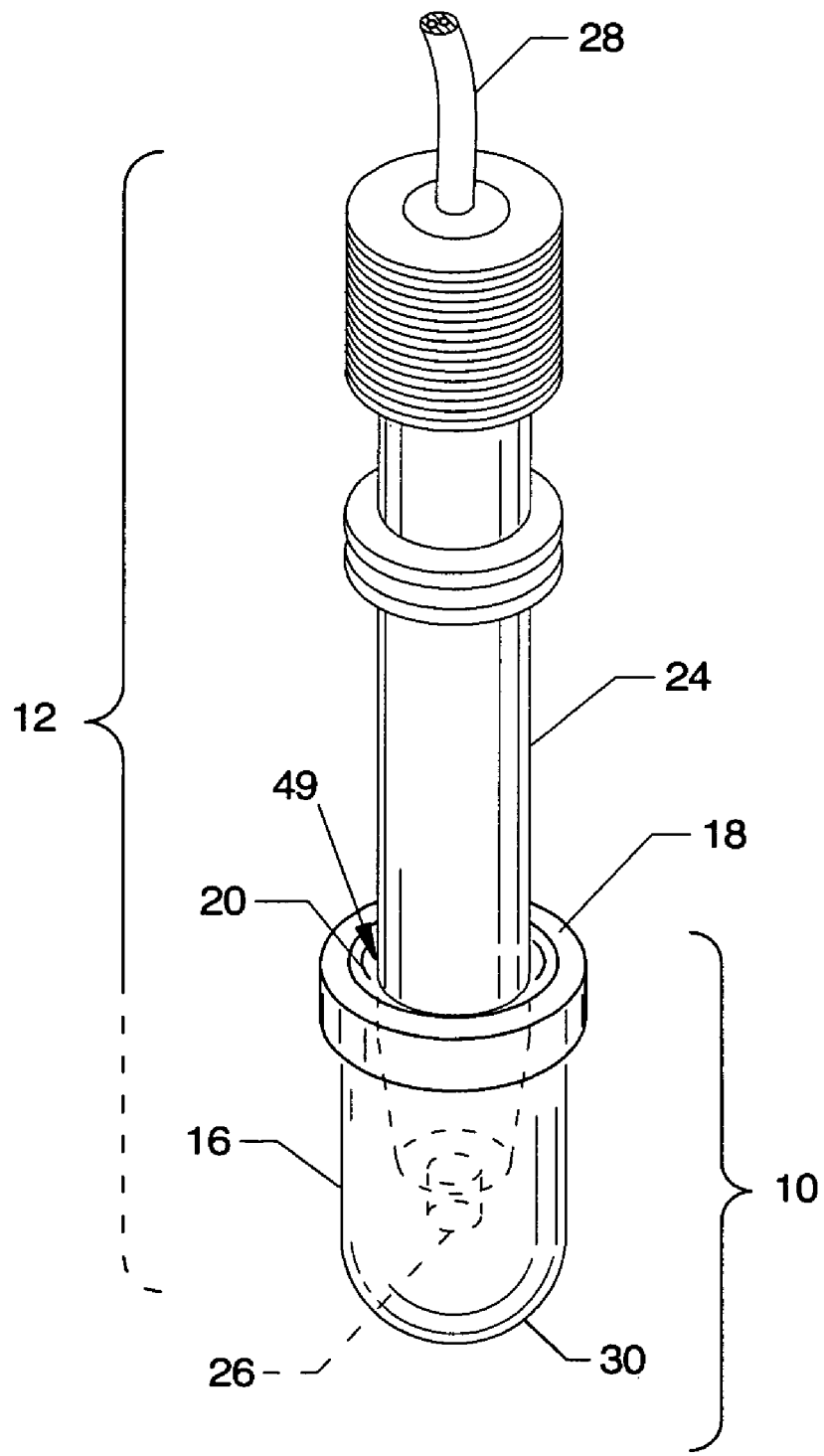
FIG. 1 is an isometric view of an immersion bag system, the present invention, shown in use surrounding the tip of an ultrasound probe.
Figure 2:
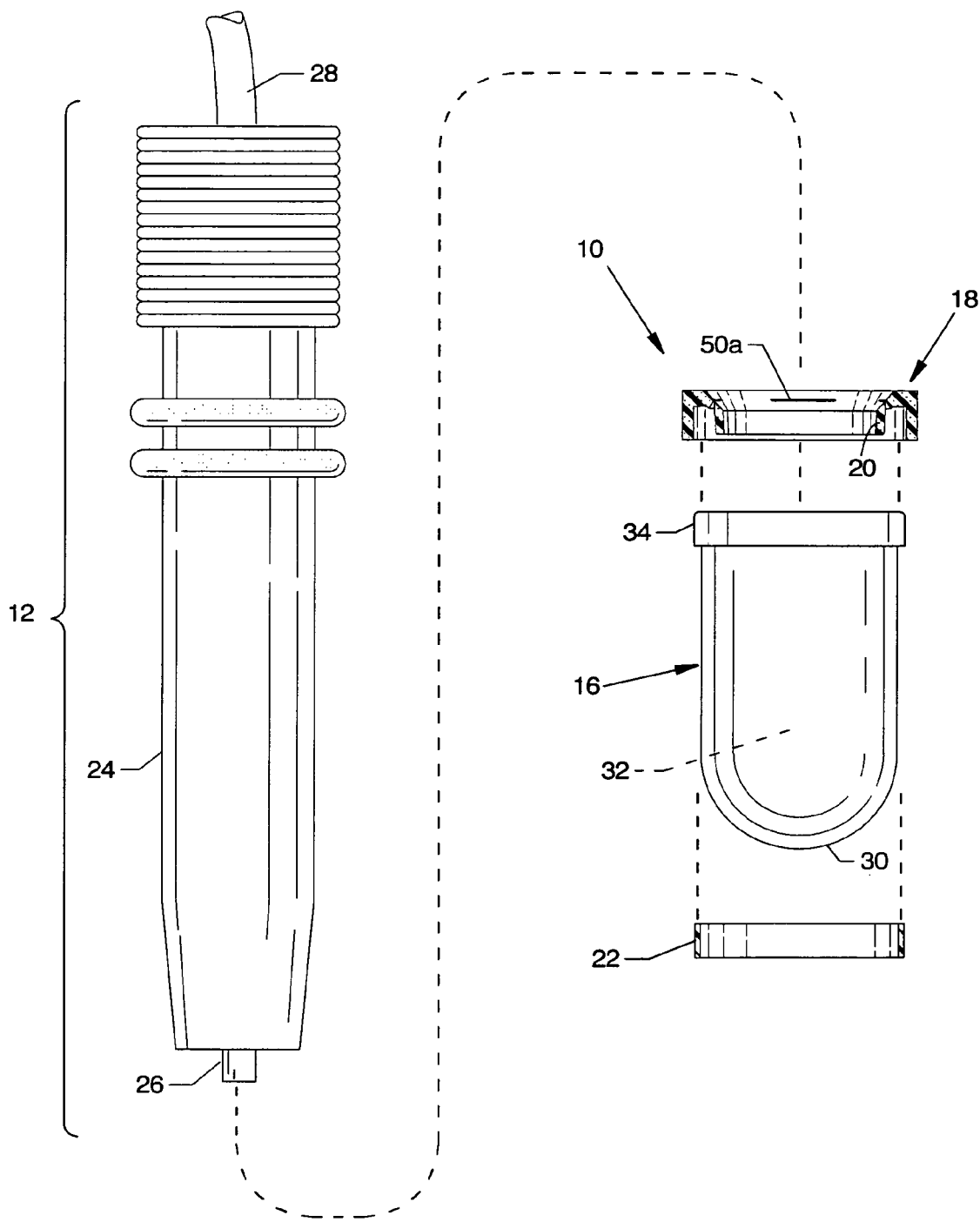
FIG. 2 is provided to show a partially exploded view of the ultrasound immersion bag system and a typical ultrasound probe for use therewith.

FIG. 1 is an isometric view of an immersion bag system 10, the present invention, shown affixed to and in use with an ultrasound probe 12. The lower region of the ultrasound probe 12 is sealed in close association with the following components comprising the immersion bag system 10, each with flexible qualities including: a flexible immersion bag 16, a flexible collar 18 having an integral flexible seal 20, and a capture ring 22 which can be rigid or semi-rigid, all of which are shown in FIG. 2. The body 24 of the ultrasound probe 12 generally is tubular in shape and includes a transducer 26 at one end and also houses other internal components associated with operation of the transducer 26. The upper region of the ultrasound probe body 24 includes suitable geometrically configured external structure about the upper region thereof. A control/power cable 28 exits from one end of the ultrasound probe 12 for connection to external support components associated with operation of the transducer 26.

FIG. 2 is a partially exploded view of the sterile immersion bag system 10 incorporated to frictionally engage the lower portion of the ultrasound body 24. The structure of the immersion bag system 10 includes the immersion bag 16, the flexible collar 18, the flexible seal 20 integral to the flexible collar 18, and the rigid or semi-rigid capture ring 22 collectively having features suitable for providing sealed communication of the immersion bag system 10 with respect to the lower portion, i.e., the body 24, of the ultrasound probe 12.

The flexible seal 20 which is integral to the flexible collar 18 is of a general annular shape each being fashioned of a flexible material, such as, but not limited to, foam, preferably close cell foam, latex, rubber, plastic, or other suitable flexible and pliable material, and includes aligned and connecting generally annular-shaped structure. Once engaged onto the ultrasound probe 12, the flexible seal 20 is watertight permitting examinations in any position (e.g., patient sitting upright or laying down).

Figure 14:
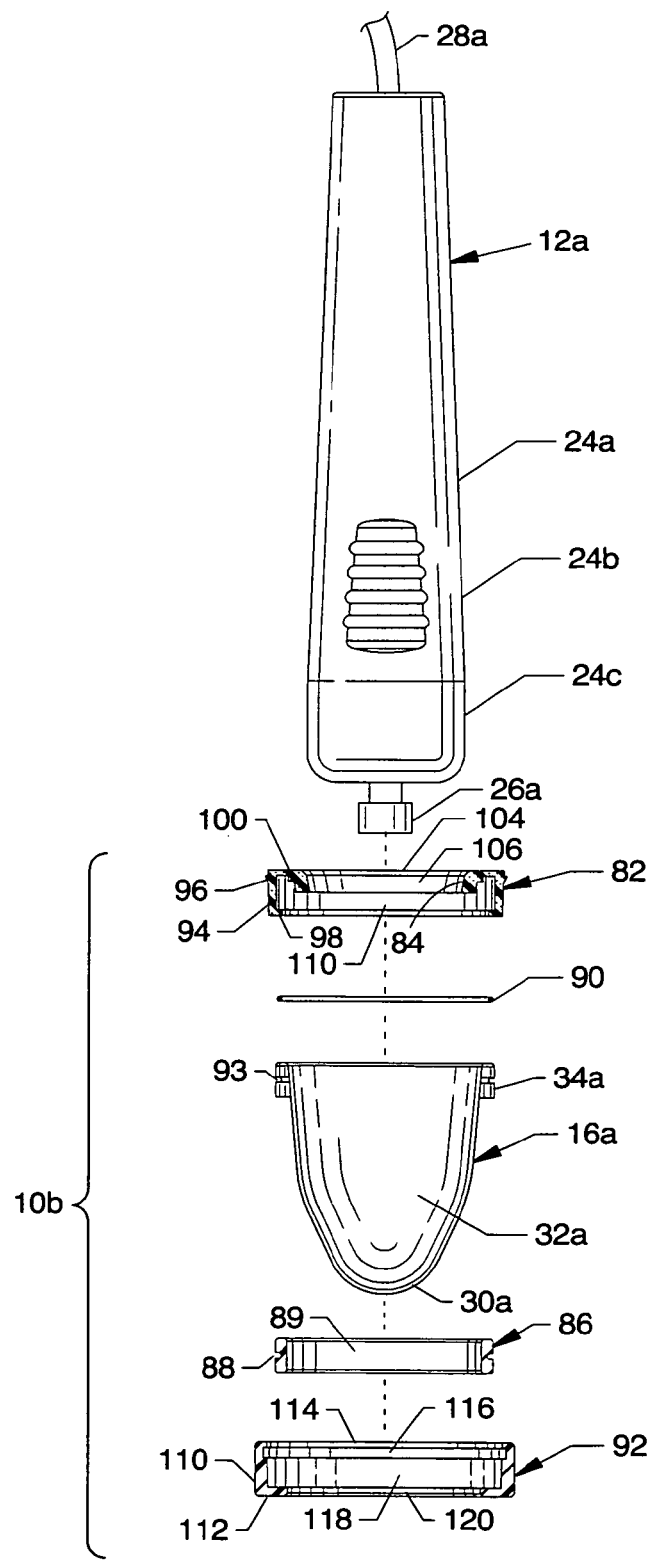
FIG. 14 is a partially exploded view of the sterile immersion bag system incorporated to frictionally engage the lower nontapered portion of the ultrasound probe.

The immersion bag 16 is formed of a thin and flexible pliable acoustically invisible material (for example and demonstration, in a range of 0.1 micron to 250 microns), such as polyethylene, hydrophilic plastic, or other suitable material, which is capable of containing a gel or other suitable medium and which allows the passage of ultrasound waves. The immersion bag 16 preferably has a general cylindrical shape for the greatest portion thereof and includes an end 30 which is dome and/or bullet shaped and also includes an interior 32. In the alternative, as shown in FIG. 14, an immersion bag 16a can have a conical shape for the greatest portion thereof and can include an end 30a which has an arcuate profile. The top of the immersion bag 16 is reversed a short distance outwardly and about itself to form a lip 34 of annular shape extending about the upper region of the immersion bag 16 for accommodation of the capture ring 22. The capture ring 22 is of a general annular shape fashioned of a rigid or semi-rigid material, such as, but not limited to, plastic, cardboard, paper or other suitable material.

Figure 3:
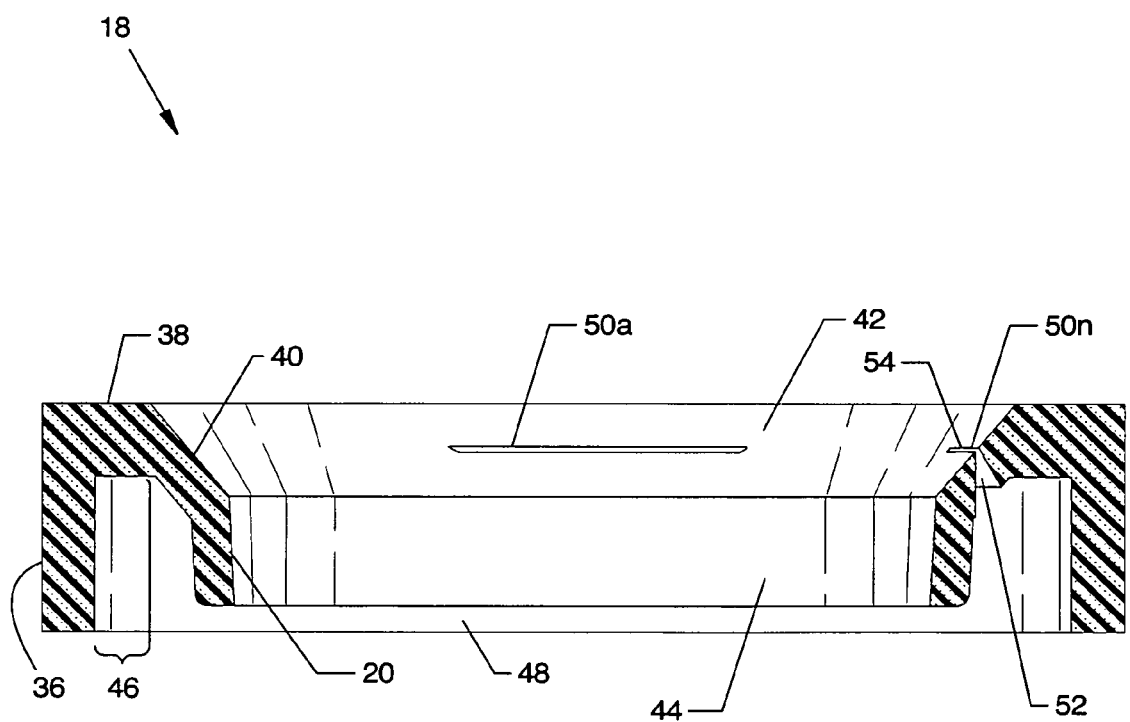
FIG. 3 is a cross section view along line 3-3 of FIG. 4 in order to show both the general structure of a flexible collar and to show valve structure extending through a flexible collar wall.
Figure 4:
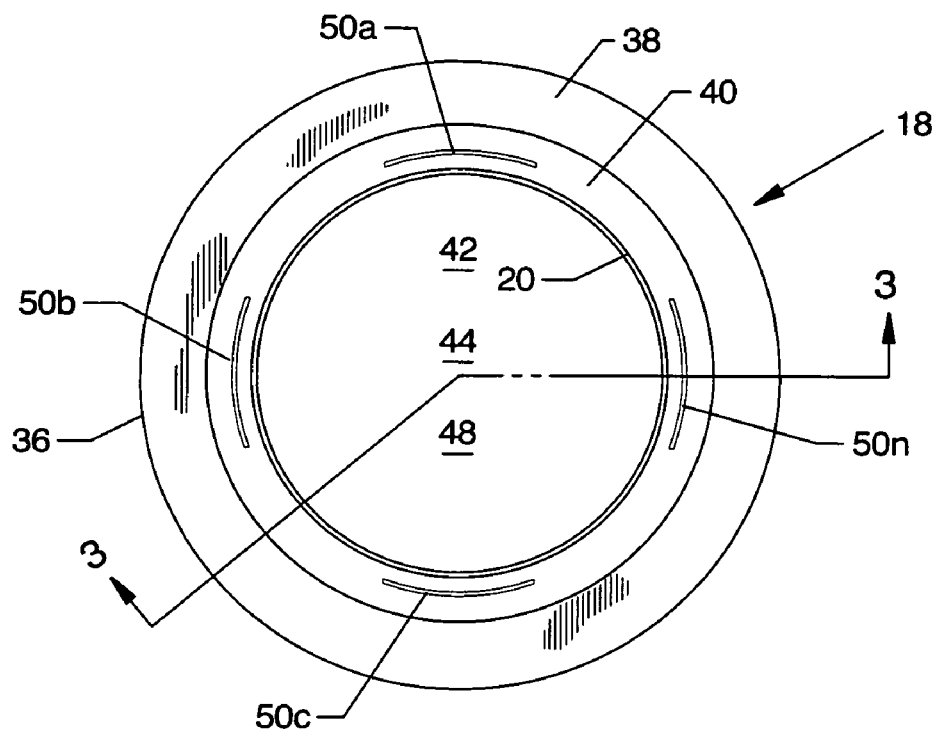
FIGS. 4 and 5 are top and bottom views, respectively, of the immersion bag flexible collar.
Figure 5:
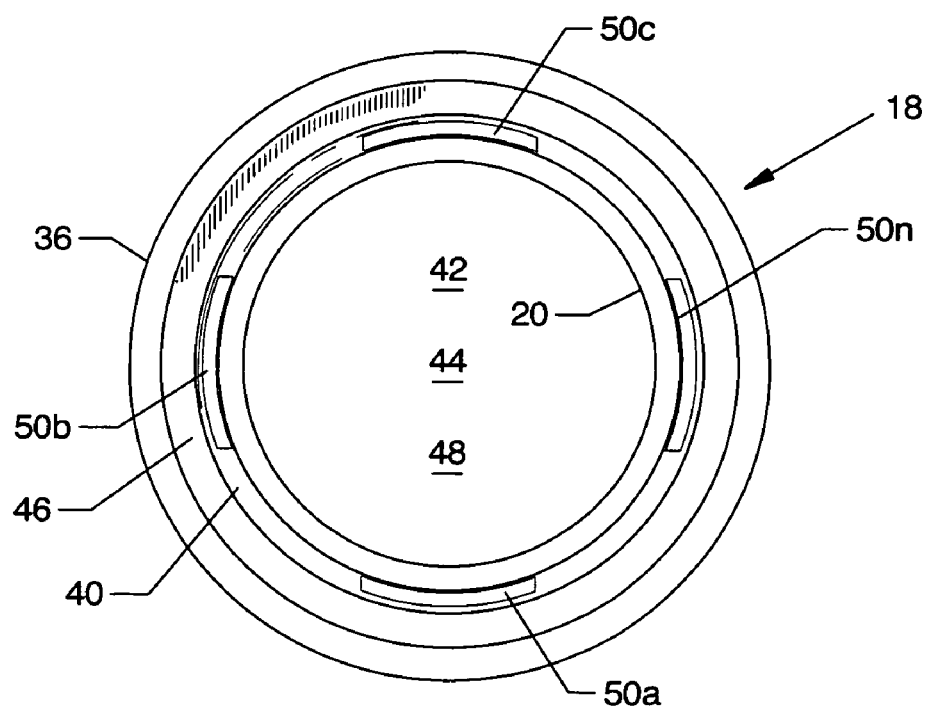
Figure 6:
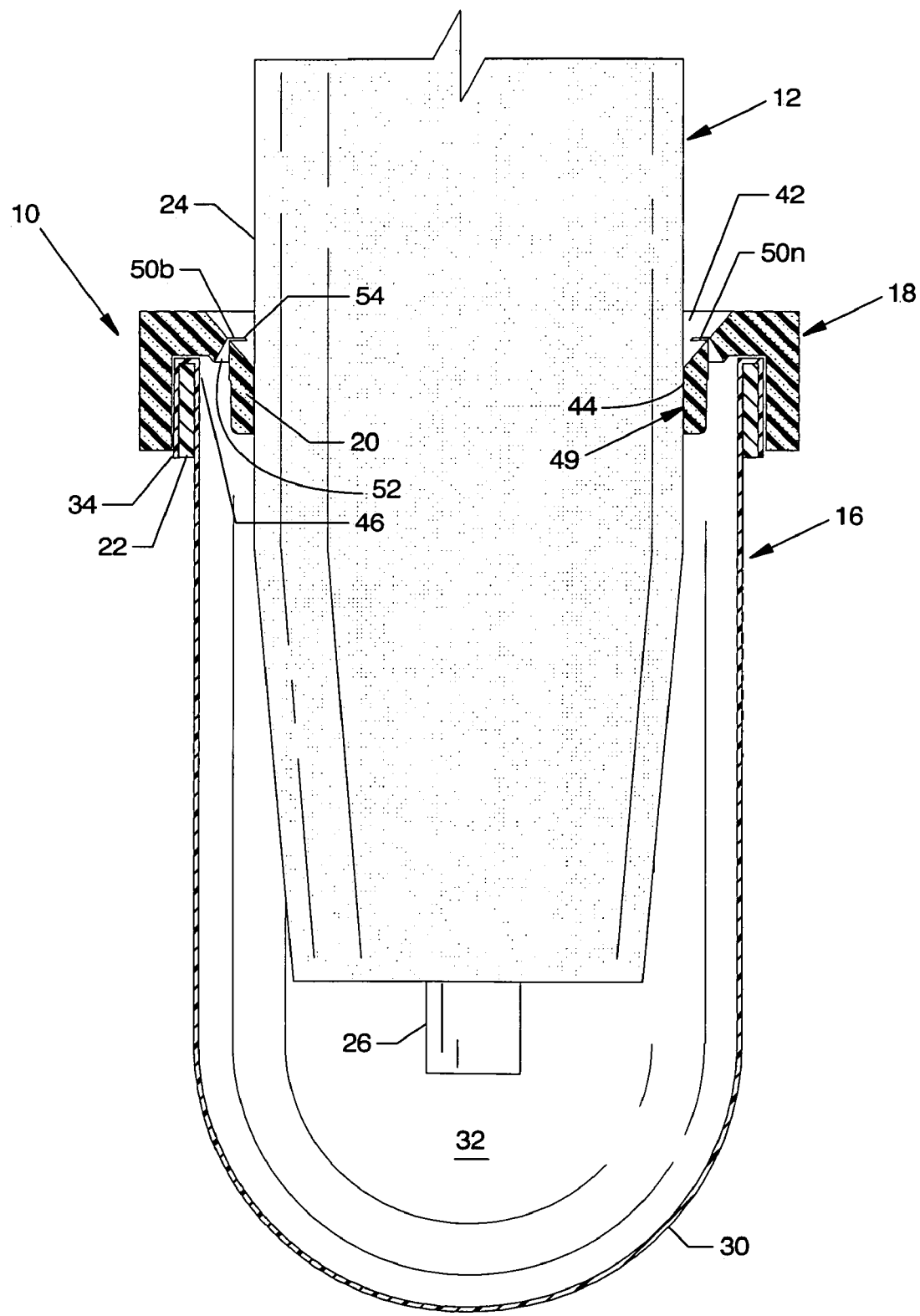
FIG. 6 is a partial cross section view showing the engagement of the immersion bag system with the tip of the ultrasound probe.

FIG. 3 is a cross section view of the one-piece flexible collar 18, also shown in detail in FIGS. 4, 5 and 6. The cross section view of FIG. 3 is taken along line 3-3 of FIG. 4 in order to show both the general structure of the flexible collar 18 and to show the structure of the valving extending through the wall thereof. The continuously formed flexible collar 18 is comprised of a plurality of geometrically configured and connecting structures including: a vertically oriented outer wall 36 which forms the periphery of the flexible collar 18, a horizontally oriented top wall 38 which intersects the upper region of the outer wall 36 and extends inwardly a short distance, an angled transition wall 40 extending inwardly and downwardly from the top wall 38 to intersect the flexible seal 20, and the flexible seal 20 extending downwardly from the lower portion of the transition wall 40. The lower portion of the flexible seal 20 is canted in slightly to ensure forcible flexed contact of the inner periphery of the flexible seal 20 with the body 24 of the ultrasound probe 12. An arrangement and the relationship of the ultrasound probe 12 with the flexible seal 20 results in an annular shaped deformable probe/seal valve 49 which is formed as shown in FIG. 6, whereby such an arrangement and relationship is perfected by the engagement of the body 24 of the ultrasound probe 12 with the inner circumference of the flexible seal 20. Other annular regions are formed by the previously described structure of the flexible collar 18 including a top opening 42 incorporating the angled inner periphery of the transition wall 40 as a guide structure for insertion of a probe body, such as the probe body 24, through the flexible collar 18 and through a middle opening 44 formed by the inner periphery of the flexible seal 20. A capture annulus 46 is formed near the junction of the inside surface of the outer wall 36 and the region underlying the top wall 38 for captured accommodation of the lip 34 of the immersion bag 16 in cooperation with the capture ring 22. An expansive bottom opening 48 is provided extending between the lower region of the capture annulus 46 and below the bottom edge of the flexible seal 20 through which an ultrasound probe body, such as the probe body 24, can pass while still maintaining slideable engagement with the flexible seal 20. One or more self-sealing valves 50a-50n of arcuate and other structure are located along, about and extending through the transition wall 40. The cross section of the self-sealing valves 50a-50n, such as shown at self-sealing valve 50n, discloses a triangular shape having an elongated arcuate opening 52 at the outwardly facing surface of the transition wall 40 narrowing to a closed but actuable elongated arcuate slit 54 at the inwardly facing surface of the transition wall 40. The triangular shape extends as an extruded arcuate shape along a suitable arc, such as 20° for the purpose of example and illustration.

FIGS. 4 and 5 are top and bottom views, respectively, of the flexible collar 18 including the flexible seal 20, the later of which when in intimate engagement with the body 24 of the ultrasound probe 12 cooperatively functions as a part of the probe/seal valve 49 itself. Shown in particular are the self-sealing valves 50a 50n in the flexible collar 18 and the annular structure of the flexible collar 18. The self-sealing valves 50a-50n vent the interior 32 of the immersion bag 16 when the tip of the ultrasound probe 12 is introduced into the interior 32 of the immersion bag 16. Air, gas, liquids, gels, or other mediums or fluids can be displaced or vented through the self-sealing valves 50a-50n during introduction of the tip of the ultrasound probe 12 or during further operation of the invention. The size of the self-sealing valves 50a-50n is shown in exaggerated form for purposes of illustration. In actual practice, the slits at the upper portions of the self-sealing valves 50a-50n, which alternatively can be in the form of narrow gaps or holes or other suitable structure, are parted by the force of the expelled or displaced air, gas, liquid, aqueous mediums, gel, or the like, and modulate toward or to a closed state upon equalization between the interior 32 of the immersion bag 16 and ambient pressure. The self-sealing valves 50a-50n could also be of different sized structure to operate across a pressure relief range. The purpose of the structure of the self-sealing valves 50a-50n is to prevent breakage of the immersion bag 16 by displacing air and to act as a fluid overflow. The self-sealing valves 50a-50n ensure adequate hydraulic force to remove wrinkles in the immersion bag 16 which result in acoustic artifacts (typically, arcuate shaped noise above the examining surface). Such hydraulic force also provides resistance so that the ultrasound probe 12 does not come into direct contact with superficial structures, such as the delicate cornea of the eye.

FIG. 6 is a partial cross section view showing engagement of the immersion bag 16 by the tip of the ultrasound probe 12. The immersion bag system 10 shown includes the flexible collar 18 including the flexible seal 20, the capture ring 22, and the immersion bag 16 fully arranged and assembled using the structural features of such components in suitable engagement made possible by the elastic qualities of the involved components in combination with the frictional engagement fixation of the lip 34 of the immersion bag 16 within the capture annulus 46 by the capture ring 22, such as by the use of heat staking, tape, an O-ring, bands (not shown) which preferably are elastic, adhesive or other suitable attachment devices or methods. The lip 34 is wrapped about and frictionally and tensionally engages to the surfaces of the capture ring 22 and then is secured within the capture annulus 46, and sealingly held against the inner surface of the outer wall 36 by the forcible positioning of and the forcible engagement of the capture ring 22. The flexible seal 20 flexes to sealingly accommodate and frictionally engage and seal against the body 24 of the ultrasound probe 12 forming the probe/seal valve 49, as previously described. The sealing integrity of the flexible seal 20 is enhanced by an increase in the internal pressure of the immersion bag 16 by introduction of the ultrasound probe 12 into the immersion bag 16, i.e., fluid pressure is exerted against the flexible seal 20, thereby uring the flexible seal 20 into tighter intimacy against the ultrasound probe 12. The tip of the ultrasound probe 12 is positioned within the interior 32 of the immersion bag 16, wherein the transducer 26 is spaced sufficiently from the end 30 of the immersion bag 16 to allow flexing of end 30 about the surface of the eye and to prevent contact of the transducer 26 with end 30 of the immersion bag during such flexing.

Mode of Operation

Figure 7:
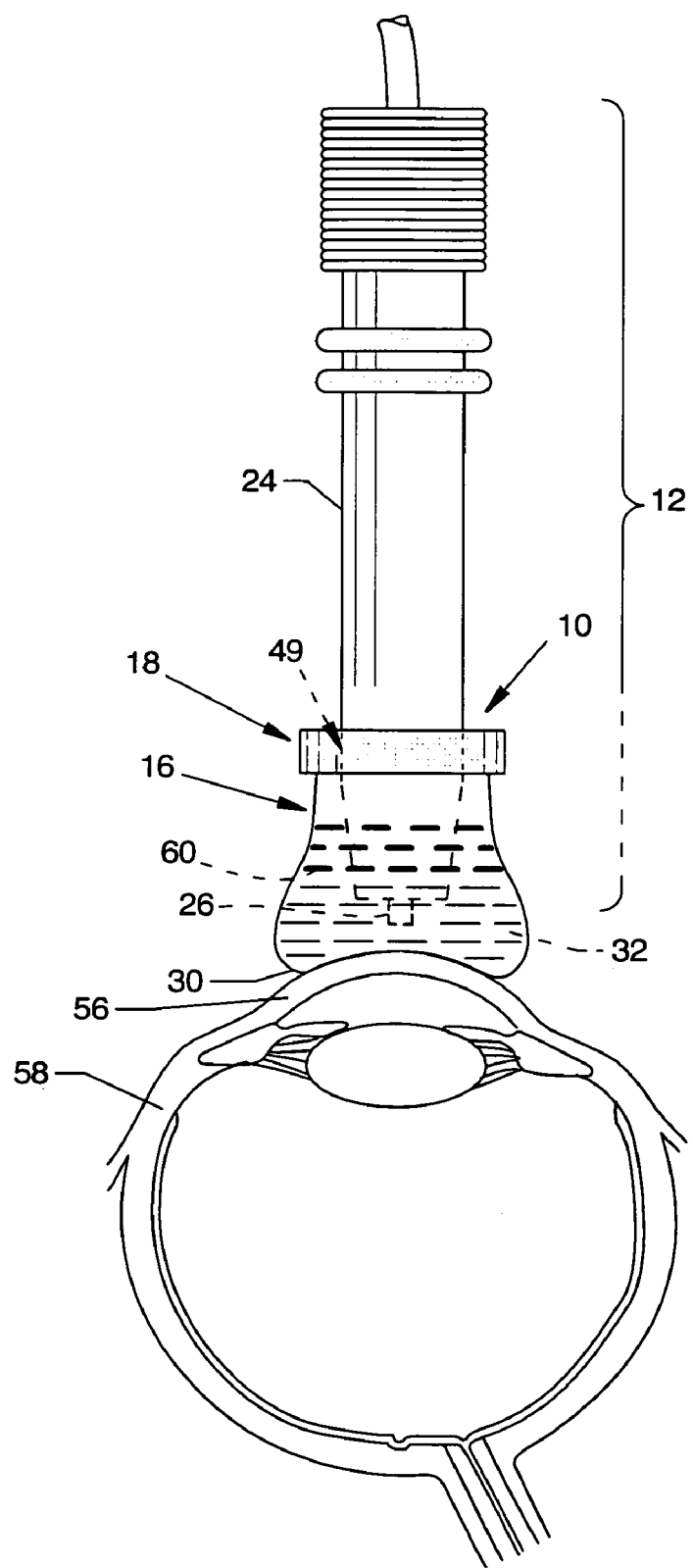
FIG. 7 illustrates a sterile immersion bag system surrounding the tip of an ultrasound probe and contacting the cornea of an eye as utilized during an ultrasound scan of the central portion of the eye and illustrating how the near field artifact is overcome.
Figure 8:
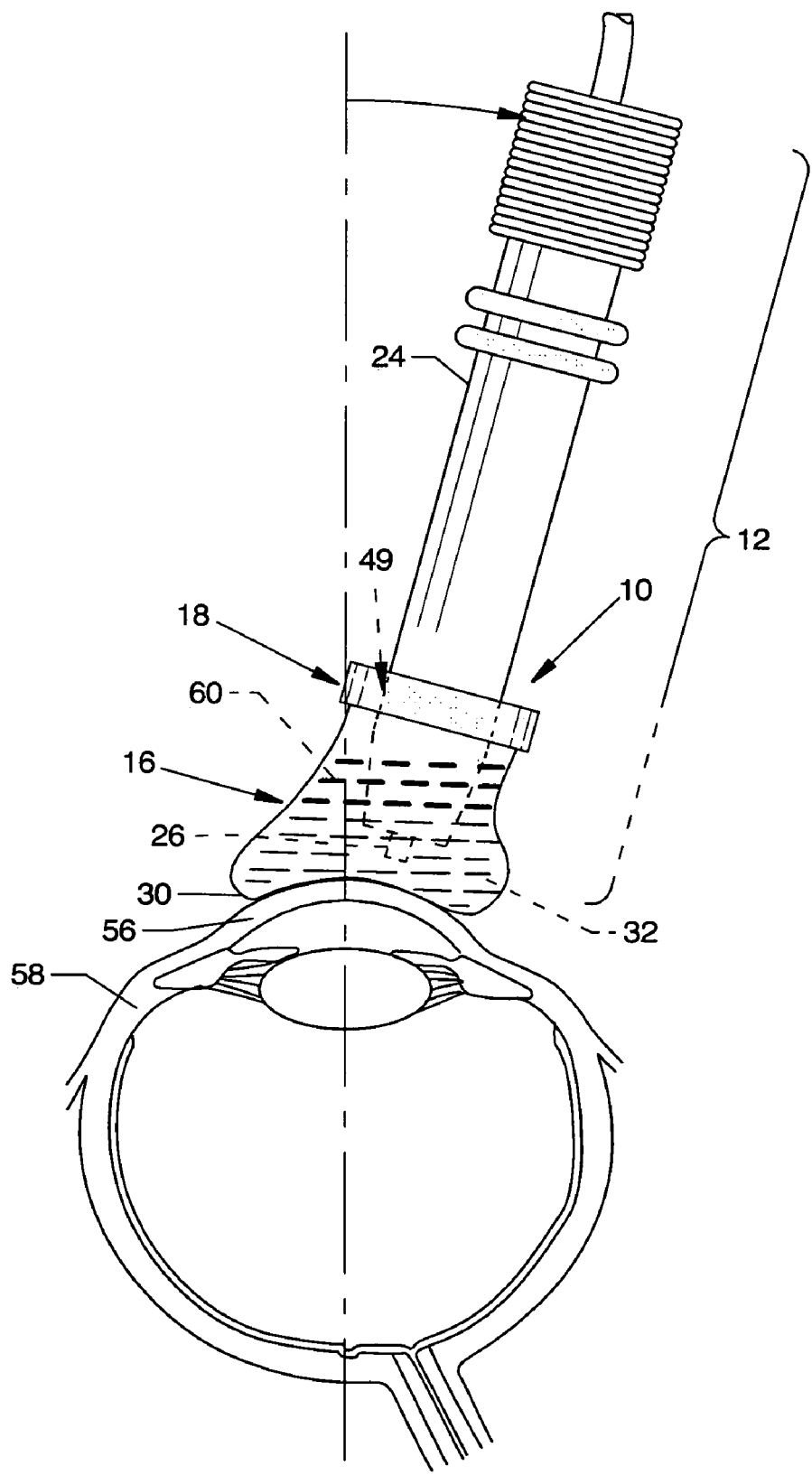
FIG. 8 illustrates the ultrasound probe with the immersion bag system in close engagement with a cornea of an eye for an ultrasound scan of a noncentral portion of the eye where the ultrasound probe is depicted at an angle within the stationary but flexible immersion bag and maintaining positive pressure to minimize the chance of damaging sensitive/delicate tissue such as the cornea of the eye.

FIGS. 7 and 8 illustrate the immersion bag system 10 in use with an ultrasound probe 12 engaging a cornea 56 of an eye 58 for an ultrasound scan, e.g., of the central and non-central aspects of the eye 58, respectively. The immersion bag system 10 can be furnished as a sterile prepackaged disposable unit. The immersion bag 16 can be manually filled with water, gel 60 or other suitable ultrasound transmission medium, such as other aqueous medium, or the immersion bag 16 can be prefilled and covered by a removable top seal to contain the gel 60 or other aqueous medium within the immersion bag 16, wherein the top seal is removed prior to introducing the end of the probe body 24 into the flexible collar 18 and into the immersion bag 16. When examining ocular structures, coupling gel on the bag outer surface is not required. This is a unique feature of this invention. However, the use of gel on the bag exterior may be considered in cutaneous or industrial applications. Also, a foil sealed external container can hold an adequate amount of transducer coupling medium external to the immersion bag 16 for manual loading. During introduction of the end of the probe body 24 into the flexible collar 18 and the immersion bag 16, the flexible seal 20 flexingly and transitionally seals against the body 24 of the ultrasound probe 12 and concurrently forms the probe/seal valve 49. This ensures that the gel 60 or other aqueous medium is contained within the interior 32 of the immersion bag 16 and positive pressure is created. By exerting sideways force, using the ultrasound probe 12 against the flexible seal 20 or by rocking or angulating the ultrasound probe 12 against the flexible seal 20, a gap is created by deforming the probe/seal valve 49 to expel excess internal pressure, air and liquid overfill allowing a reduction in immersion bag internal pressure to a desired level and a desired bag shape. The previously described self-sealing valves 50a-50n are parted when the internal pressure of the immersion bag 16 exceeds a certain level in order to maintain the integrity of the immersion bag 16 and releases enough air, gas, liquid, gel, or other aqueous medium to reduce the internal pressure of the immersion bag 16 to a safe level and to prevent the immersion bag 16 from denting the cornea in an eye having low pressure, while still maintaining a suitable internal positive pressure within the immersion bag 16. The ultrasound probe 12 is introduced a suitable distance (depending on probe transducer frequency) into the interior 32 of the immersion bag 16 filled with gel 60 or other aqueous medium to overcome near field artifact where the transducer 26 preferably maintains a suitable spacing from the immersion bag end 30 and thus from the cornea 56 or other near surface where the possibility of direct contact with structures under examination are minimized. The distal end of the invention, i.e., the immersion bag 16, comes in direct contact with the cornea 56 or other superficial structure, and upon initial contact, the end 30 of the immersion bag 16 intimately contacts and begins conformal reshaping to and about the surface of the cornea 56 or other superficial structure, while yet maintaining suitable spacing between the transducer 26 and the cornea 56 to overcome near field artifact. Also, the immersion bag 16 conforms to the surface under examination whether regular or irregular. The external ultrasound equipment is then energized after the ultrasound probe 12 is placed into the immersion bag 16 containing liquid/gel that has coupling fluid on the inside enabling an ultrasound scan of suitable width across the anterior aspects of the eye or other superficial structure. An ultrasound scan across a noncentral portion of the eye 58, such as the sclera or white of the eye or other superficial structure, can be accomplished, such as shown in FIG. 8, where the ultrasound probe 12 and the flexible collar 18 is unitarily repositioned off center and to the side of the immersion bag 16 while maintaining the central original end 30 point of mutual contact. Contact with the examining surface remains in intimate contact due to the flexible nature of the immersion bag 16. Thus, there is minimal drag across sensitive and delicate structures such as the cornea, reducing the chance of abrasion. Although the invention is described for use with an eye, the principles of the invention also apply to use about other superficial areas of a body whether human, animal for ocular, cutaneous or vascular purposes or inanimate objects such as tubing carrying fluid. When the ultrasound probe 12 is inserted through the flexible collar 18, the flexible seal 20 will be pulled downwardly, whereby this action will open one or more of the self-sealing valves 50a-50n. Concurrently, the flexible seal 20 can function as a deformed component of the probe/seal valve 49 by forcing the ultrasound probe 12 against the flexible seal 20 in one or another direction or by angulation or by rocking thereby deforming the probe/seal valve 49 and creating one or more gaps at the flexible seal. Thus, as the ultrasound probe 12 is moved into position as it is inserted into the immersion bag 16, a slight pressure is maintained as the ultrasound probe 12 stops moving downwards, whereby excess filler gel/liquid or air has been simultaneously displaced. By angulating and/or forcing the body of the ultrasound probe 12 against one side of the probe/seal valve 49, one or more gaps can be created (such as gap 122 shown in FIGS. 22 and 23 of an alternative embodiment), thereby opening the probe/seal valve 49 to release internal pressure, trapped air and/or excess fluid.

Figure 9:
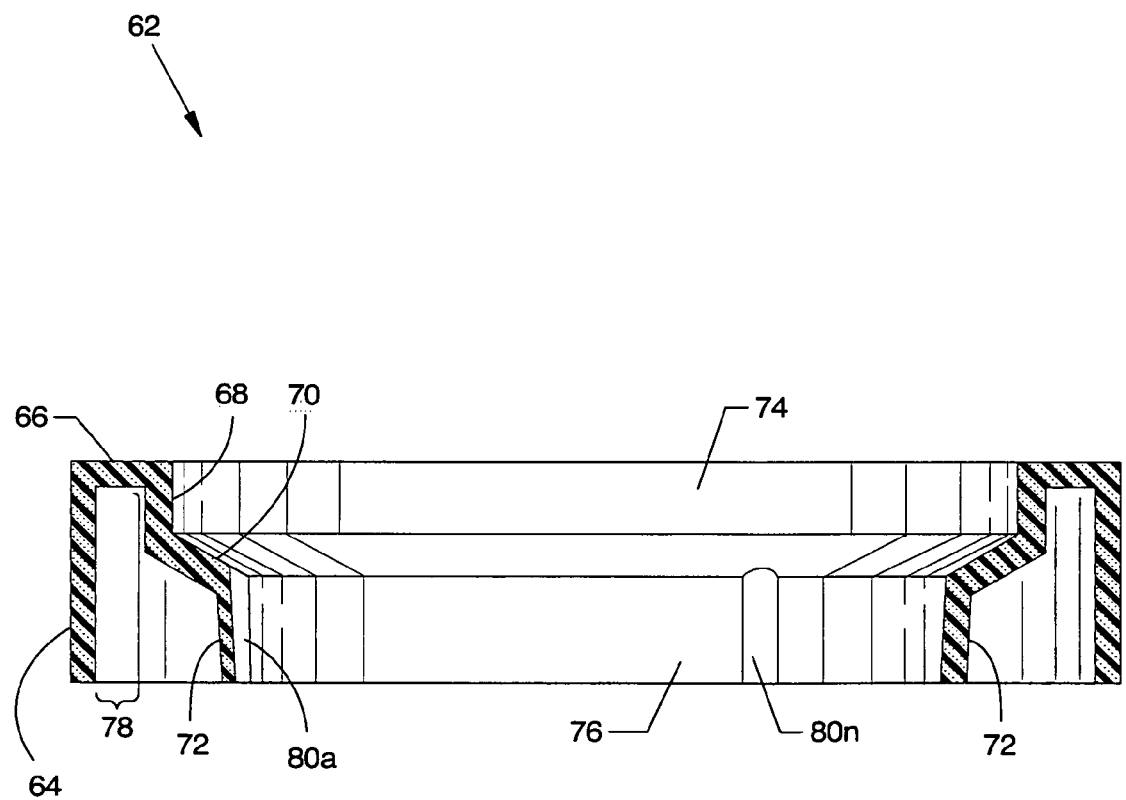
FIG. 9, an alternative embodiment, is a cross section view of a one-piece flexible collar.
Figure 10:
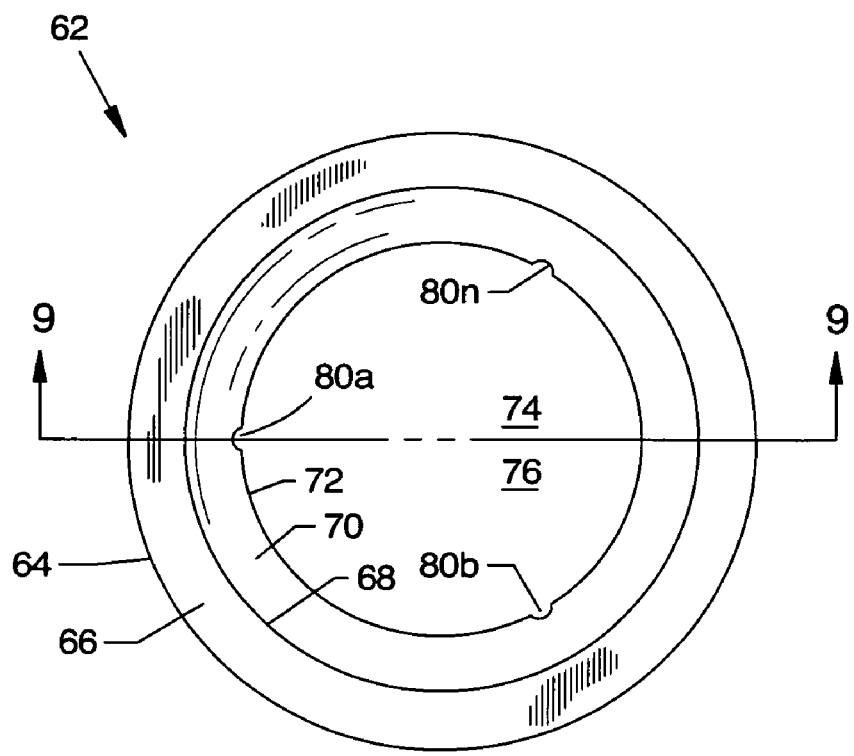
FIGS. 10 and 11 are top and bottom views, respectively, of the one-piece flexible immersion bag.
Figure 11:
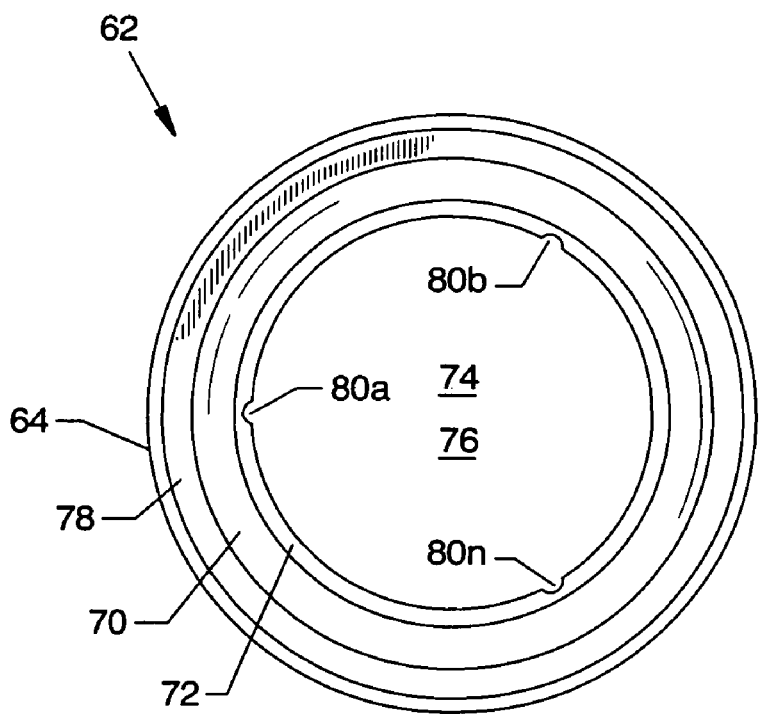
Figure 12:
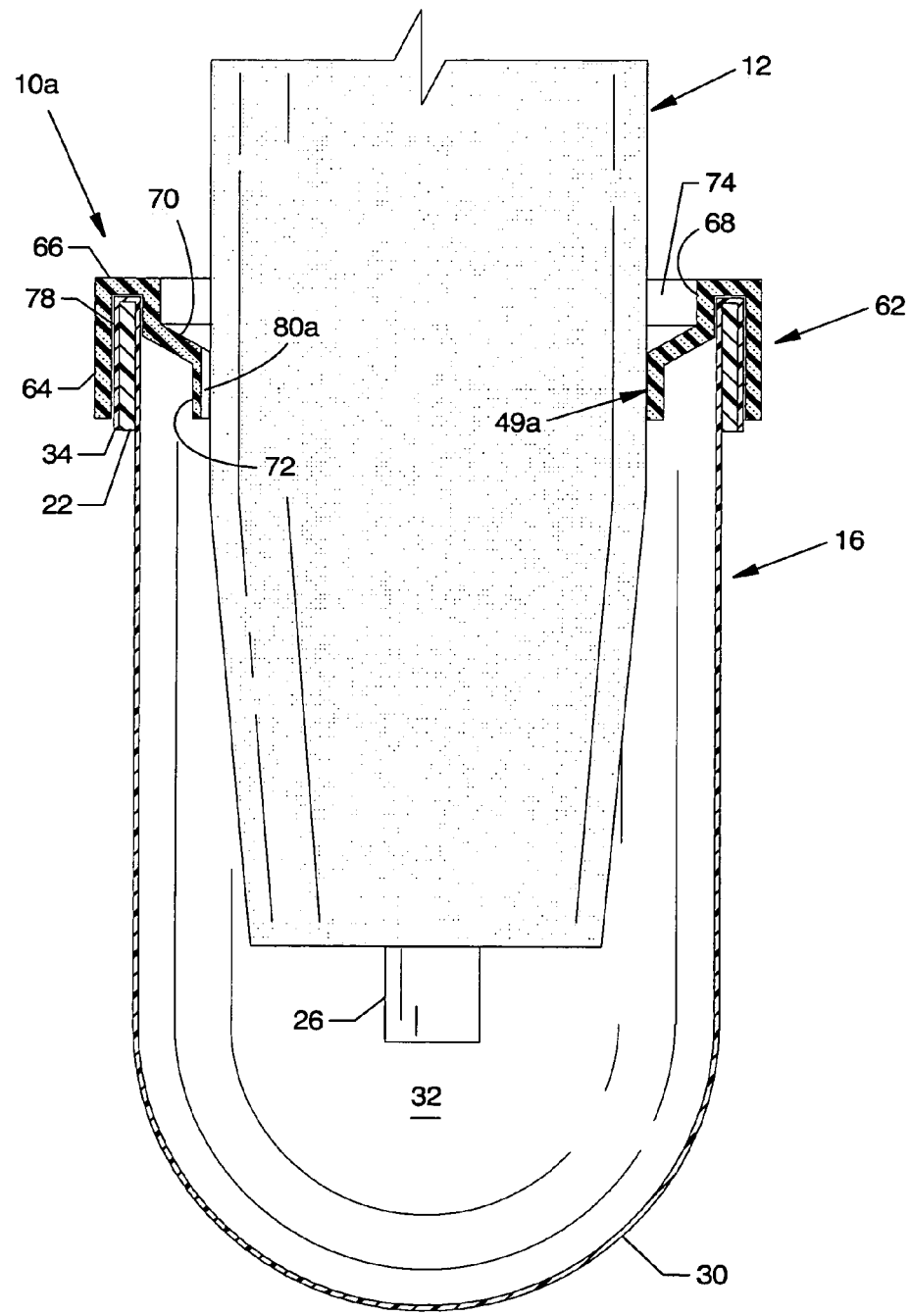
FIG. 12 is a partial cross section view showing engagement of the immersion bag system by the tip of the ultrasound probe.

FIG. 9 is a cross section view of a one-piece flexible collar 62 for use with an immersion bag system 10a, an alternative embodiment, also shown in detail in FIGS. 10, 11 and 12. The flexible collar 62 is of a general annular shape fashioned preferably of a flexible material, such as foam, preferably close cell foam, latex, rubber or of other suitable flexible and pliable materials. The cross section view of FIG. 9 is taken along line 9-9 of FIG. 10 in order to show both the general structure of the flexible collar 62 and to show the structure of the valving extending through the wall thereof. The continuously formed flexible collar 62 is comprised of a plurality of geometrically configured and connecting structures including a vertically oriented outer wall 64 which forms the periphery of the flexible collar 62, a horizontally oriented top wall 66 which intersects the upper region of the outer wall 64 and extends inwardly a short distance, a vertically oriented inner wall 68 extending downwardly from the top wall 66, and an angled transition wall 70 extending inwardly and downwardly from the lower portion of the inner wall 68 and a downwardly extending seal flexible 72 extending from the angled transition wall 70. The lower portion of the flexible seal 72 can be canted in slightly to ensure forcible flexed contact of the inner periphery of the flexible seal 72 with the body 24 of the ultrasound probe 12. Other annular regions are formed by the previously described structure of the flexible collar 62 including a top opening 74 incorporating the angled inner periphery of the transition wall 70 and the inner periphery of the inner wall 68 as a guide structure for insertion of a probe body, such as the probe body 24, through the flexible collar 62, and a bottom opening 76 formed by the inner periphery of the flexible seal 72. A capture annulus 78 is formed near the junction of the inside surface of the outer wall 64 and the region underlying the top wall 66 for captured accommodation of the lip 34 of the immersion bag 16 in cooperation with the capture ring 22. One or more self-sealing valves 80a-80n, preferably of arcuate structure, are located along, about and extending vertically through the inner face of the flexible seal 72. The cross section of the self-sealing valves 80a 80n, such as shown at self-sealing valve 80a, discloses an elongated arcuate structure. The self-sealing valves 80a-80n are shown in the open position, such as when venting excess pressures or fluid medium therethrough. In the nonventing position, the shape of the self-sealing valves 80a-80n would assume a flattened position against the body 24 of the ultrasound probe 12, but would modulate toward the open position during releasing of pressure or of fluid medium.

FIGS. 10 and 11 are top and bottom views, respectively, of the flexible collar 62, including the flexible seal 72. Shown in particular are the self-sealing valves 80a-80n in the flexible collar 62 and the annular structure of the flexible collar 62. The self-sealing valves 80a-80n vent the interior 32 of the immersion bag 16 when the tip of the ultrasound probe 12 is introduced into the interior 32 of the immersion bag 16. Air, gas, liquids, gels, or other mediums or fluids can be displaced or vented through the self-sealing valves 80a-80n during introduction of the tip of the ultrasound probe 12 or during further operation of the invention. The size of the self-sealing valves 80a-80n is shown in exaggerated form for purposes of illustration. In actual practice, the option of additional self-sealing valves 50a-50n, which alternatively can be in the form of narrow gaps, slits or of related shape decreasing geometry structure or other suitable structure, are parted by the force of the expelled or displaced air, gas, liquid, aqueous mediums, gel, or the like, and modulate toward or to a closed state upon equalization between the interior 32 of the immersion bag 16 and ambient pressure. The self-sealing valves 80a-80n could be of different sized structure to operate across a pressure relief range. The purpose of the structure of the self-sealing valves 80a-80n or optional/additional self-sealing valves 50a-50n is to allow examination of eyes with low pressure by displacing air and to act as a fluid overflow. The self-sealing valves 80a-80n ensure adequate hydraulic force to remove wrinkles in the immersion bag 16 which result in acoustic artifacts (typically, arcuate shaped noise above the examining surface). Such hydraulic force also provides resistance so that the ultrasound probe 12 is prevented from coming into direct contact with the cornea of the eye.

FIG. 12 is a partial cross section view showing engagement of the immersion bag 16 by the tip of the ultrasound probe 12. The immersion bag system 10a shown includes the flexible collar 62, including the flexible seal 72, the capture ring 22, and the immersion bag 16 fully arranged and assembled using the structural features of such components in suitable engagement made possible by the elastic qualities of the involved components in combination with the fixation of the lip 34 of the immersion bag 16 within the capture annulus 78 by the capture ring 22 using heat staking, adhesive or other suitable attachment, as described in a previous embodiment. Additionally, the lip 34 of the immersion bag 16 is secured in the capture annulus 78 and sealingly held against the inner surface of the outer wall 64 by the forcible positioning of and the forcible engagement of the capture ring 22. The flexible seal 72 flexes to sealingly accommodate and frictionally engage and seal against the body 24 of the ultrasound probe 12 in the formation of the probe/seal valve 49a. The tip of the ultrasound probe 12 is positioned within the interior 32 of the immersion bag 16, wherein the transducer 26 is spaced sufficiently from the end 30 of immersion bag 16 to allow flexing of the end 30 in a spaced relationship with the eye and to prevent contact of the transducer 26 with the end 30 of immersion bag 16 during such flexing. The mode of operation of this first alternative embodiment is substantially the same as described for the immersion bag system 10, the only difference being that the flexible collar 62 is substituted for the flexible collar 18.

Figure 13:
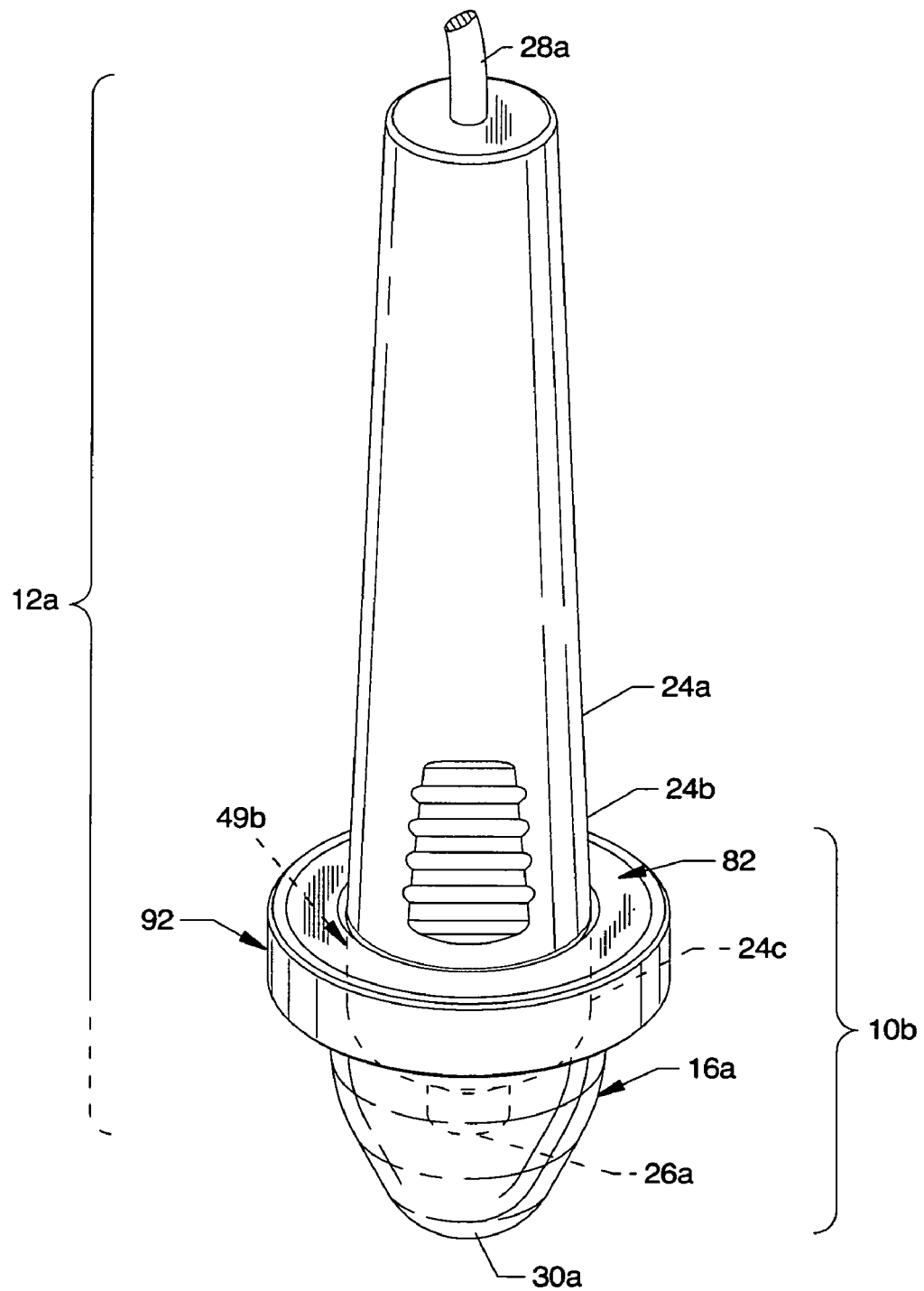
FIG. 13, an alternative embodiment, is an isometric view of an immersion bag system shown affixed to and in use with another form of the ultrasound probe.

FIG. 13 is an isometric view of an immersion bag system 10b, an alternative embodiment, shown affixed to and in use with another form of the ultrasound probe 12, herein designated as ultrasound probe 12a. The lower region of the ultrasound probe 12a is sealed in close association with the following components comprising the immersion bag system 10b each with flexible or semi-rigid qualities including: an immersion bag 16a, a flexible collar 82 having an integral flexible seal 84, and a capture ring 86 which can be rigid or semi-rigid having an annular groove 88 and an opening 89, each of which are shown in FIG. 14. The lower region of the ultrasound probe 12a also closely associates with other components of the immersion bag system 10a, including an O-ring 90, preferably having flexible qualities, and a rigid maneuvering ring 92, each of which are also shown in FIG. 14. The body 24a of the ultrasound probe 12a is, for the most part, a tapered tubular structure including tapered body section 24b and a nontapered body section 24c, and includes a transducer 26a at one end and also houses other internal components associated with operation of the transducer 26a. A control/power cable 28a exits from one end of the ultrasound probe 12a for connection to external support components associated with operation of the transducer 26a.

FIG. 14 is a partially exploded view of the sterile immersion bag system 10b incorporated to frictionally engage the nontapered body section 24c of the ultrasound body 24a of the ultrasound probe 12a. The structure of the immersion bag system 10b includes the immersion bag 16a, the flexible collar 82, the flexible seal 84 integral to the flexible collar 82, the capture ring 86 which can be rigid or semi-rigid, the O-ring 90 and the maneuvering ring 92, collectively, having features suitable for providing sealed communication and/or maneuvering of the immersion bag system 10b with respect to the lower portion, i.e., the nontapered body section 24c of the ultrasound probe 12a.

The flexible seal 84, which is integral to the flexible collar 82, is of a general annular shape, each being fashioned of a flexible material, such as, but not limited to, foam, preferably close cell foam, latex, rubber, plastic, or other suitable flexible and pliable material, and includes aligned and connecting generally annular-shaped structure. Once engaged onto the nontapered body section 24c of the ultrasound probe 12a, the flexible seal 84 is watertight permitting examinations in any position (e.g., patient sitting upright or laying down).

The immersion bag 16a is formed of a thin and flexible pliable acoustically invisible material (for example and demonstration, in a range of 0.1 micron to 250 microns), such as polyethylene, hydrophilic plastic or other suitable material which is capable of containing a gel or other suitable medium and which allows the passage of ultrasound waves. The immersion bag 16a preferably is substantially a conical shape for the greatest portion thereof and includes an end 30a which is arcuate in profile and also includes an interior 32a. The top of the immersion bag 16a is reversed a short distance outwardly and about itself to form a lip 34a of annular shape extending about the upper region of the immersion bag 16a for accommodation of the capture ring 86. The lip 34a is shown as it would subsequently appear when affixed over and around, and forced and depressed into the annular groove 88 of the capture ring 86 by the O-ring 90, thereby forming an inwardly directed annular depression 93 thereabout, such as when securing the lip 34a of the immersion bag 16a to the capture ring 86. A suitable size small band may be substituted for use in lieu of the O-ring 90, whereby the band can be used to depress the lip 34a into the annular groove 88 of the capture ring 86 to form the annular depression 93, or the band can be of greater vertical proportion to forcibly direct the broad portion of the lip 34a against outer periphery of the capture ring 86 to connect the lip 34a of the immersion bag 16a to the capture ring 86. The O-ring 90 or the described bands and the capture ring 86 may also be used in the previously described embodiments to fasten the lip 34 of the immersion bag 16 to the capture ring 22. The capture ring 86 is of a general annular shape fashioned of a rigid or semi-rigid material, such as, but not limited to, plastic or other suitable material.

Figure 15:
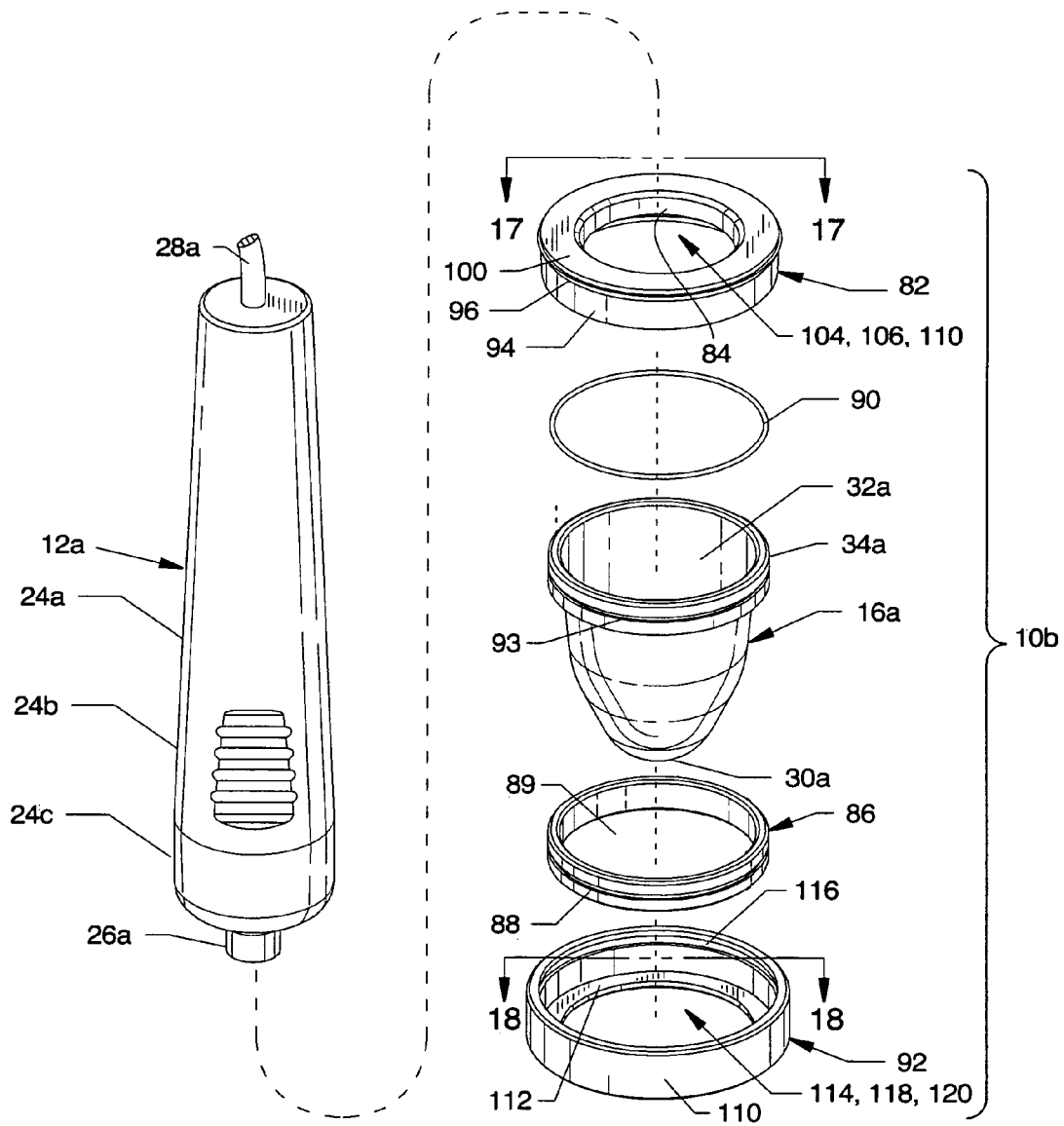
FIG. 15 is an exploded isometric top view of the immersion bag system shown distanced from the ultrasound probe.
Figure 16:
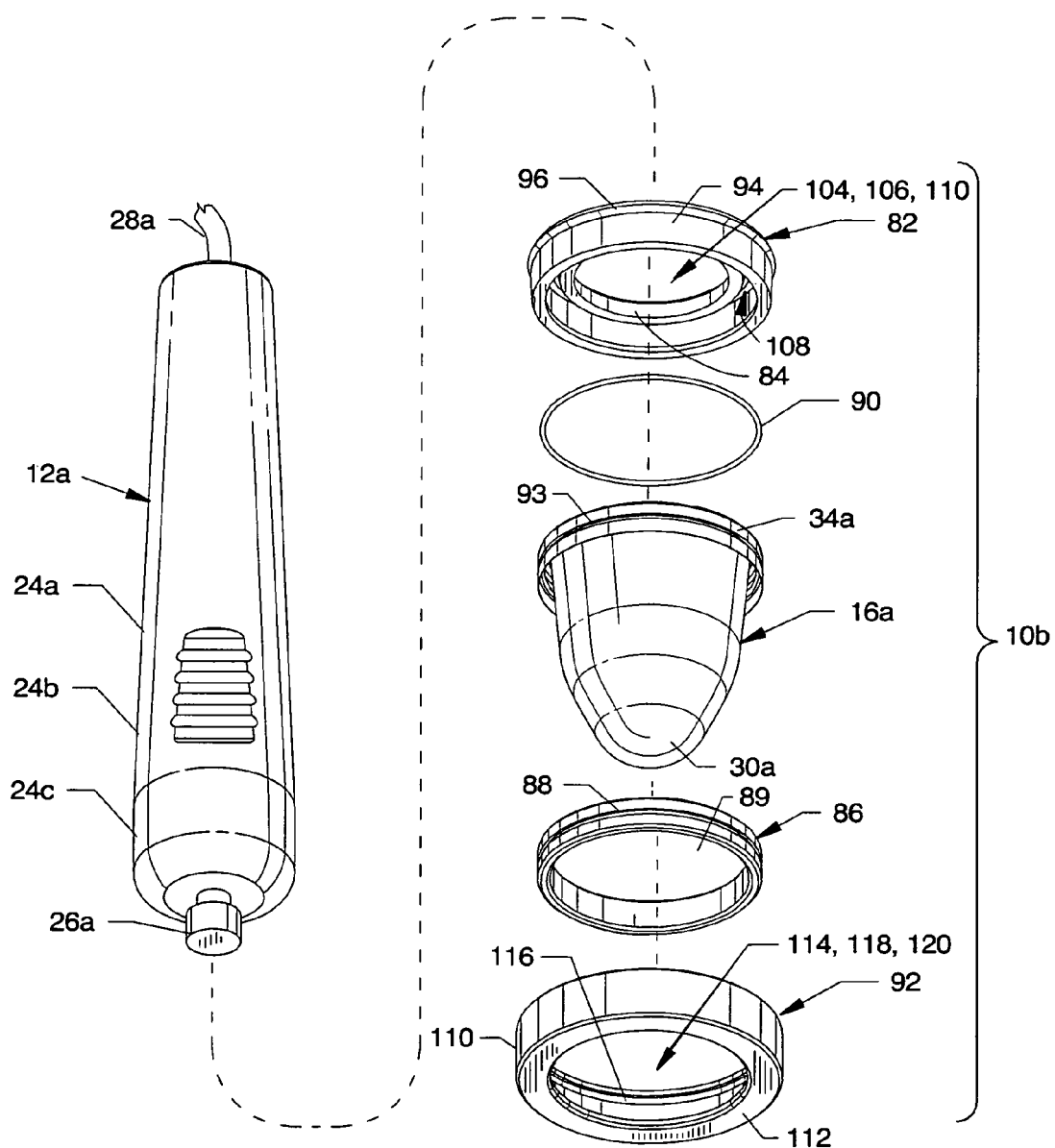
FIG. 16 is an exploded isometric bottom view of the immersion bag system shown distanced from the ultrasound probe.

FIG. 15 is an exploded isometric top view of the immersion bag system 10b shown distanced from the ultrasound probe 12a, and FIG. 16 is an exploded isometric bottom view of the immersion bag system 10b shown distanced from the ultrasound probe 12a.

Figure 17:
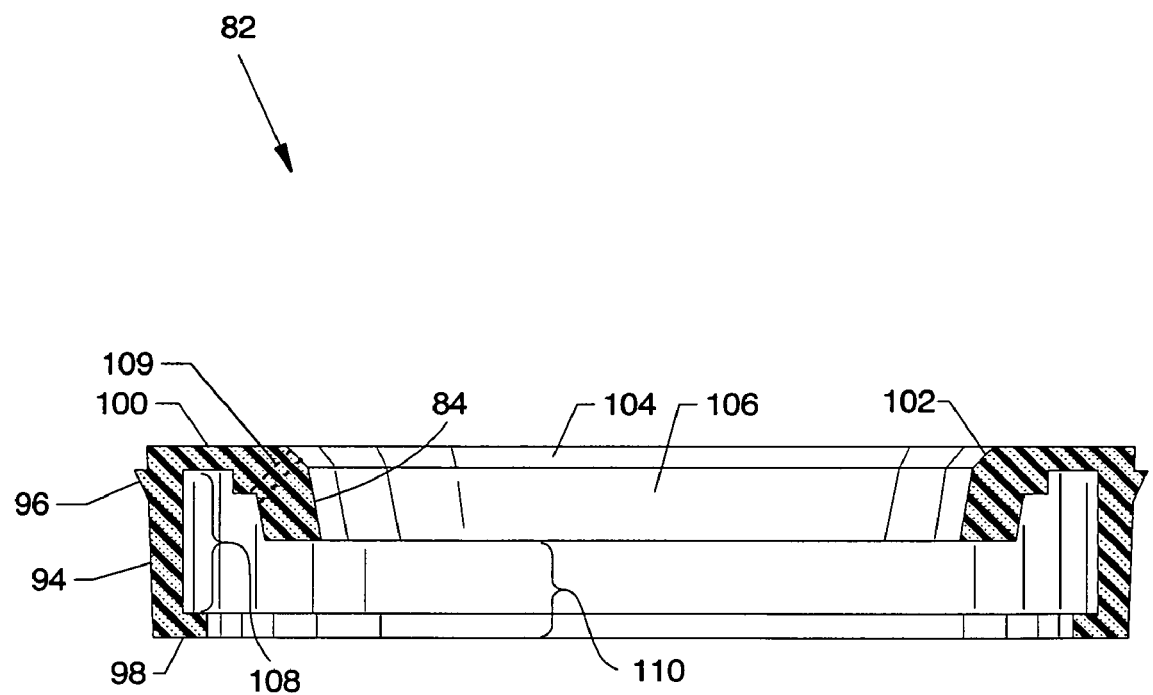
FIG. 17 is a cross section view of the one-piece flexible collar shown in FIGS. 15 and 16 along line 17-17 of FIG. 15 in order to show the general structure of the flexible collar.
Figure 21:
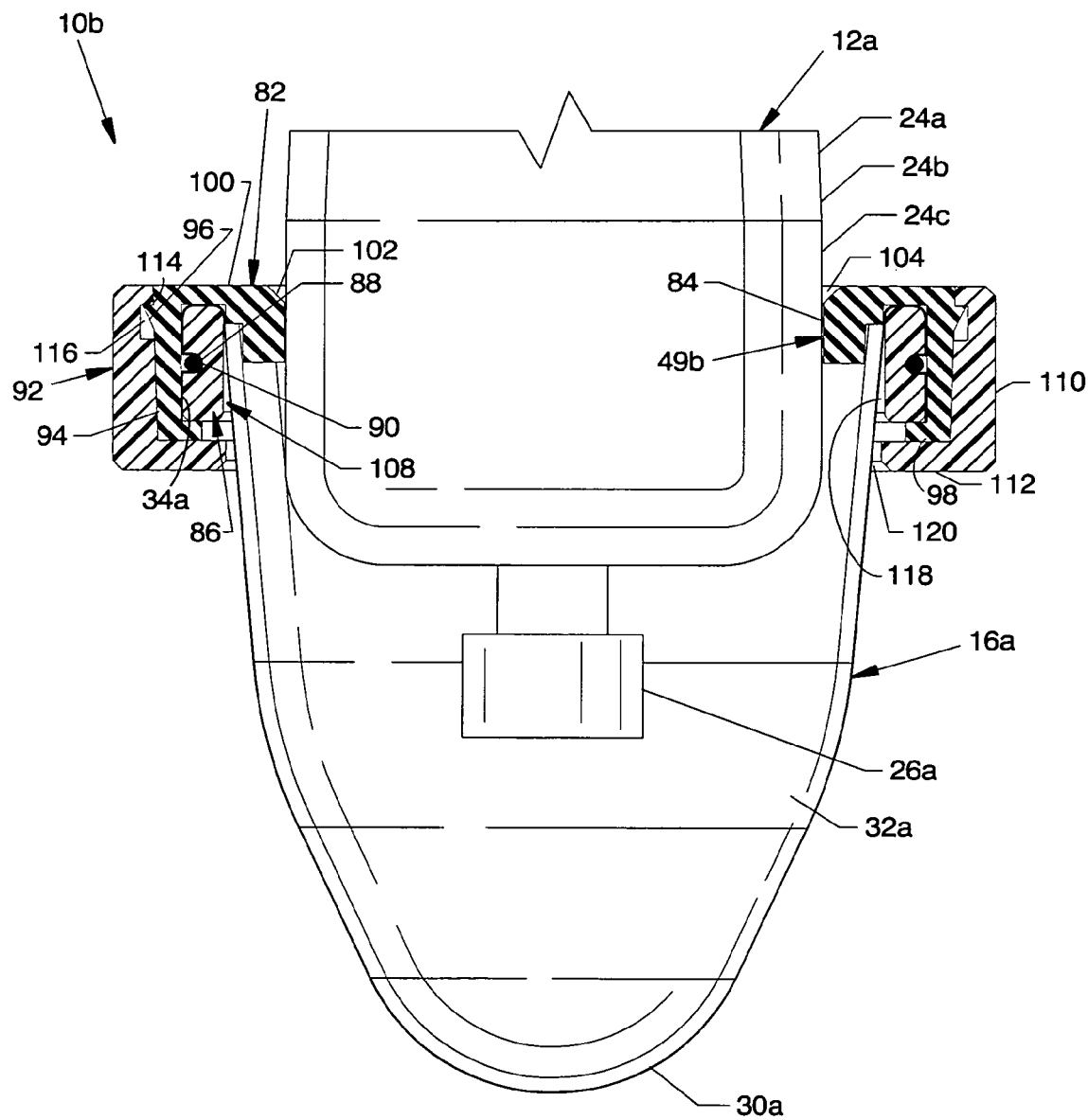
FIG. 21 is a partial cross section view showing engagement of the immersion bag system by the tip of the ultrasound probe.

FIG. 17 is a cross section view of the one-piece flexible collar 82, also shown in FIGS. 15 and 16, taken along line 17-17 of FIG. 15 in order to show the general structure of the flexible collar 82. The continuously formed flexible collar 82 is comprised of a plurality of geometrically configured and connecting structures including a vertically oriented outer wall 94 having an externally located annular ring 96 which has a beveled profile forming the periphery of the flexible collar 82, a horizontally oriented bottom wall 98 which is annular and which intersects the lower region of the outer wall 94 and extends inwardly a short distance, a horizontally oriented top wall 100 which intersects the upper region of the outer wall 94 and extends inwardly a short distance, an angled transition wall 102 extending inwardly and downwardly from the top wall 100 to intersect the flexible seal 84, and the flexible seal 84 extending downwardly and inwardly from the lower portion of the transition wall 102. The lower portion of the flexible seal 84 is canted in slightly to ensure forcible flexed contact of the inner periphery of the flexible seal 84 with the nontapered body section 24c of the ultrasound probe 12a. An arrangement and relationship of the ultrasound probe 12a with the flexible seal 84 results in an annular shaped deformable probe/seal valve 49b which is formed as shown in FIG. 21, whereby such an arrangement and relationship is perfected by the engagement of the nontapered body section 24c of the body 24a of the ultrasound probe 12a with the inner circumference of the flexible seal 84. Other annular regions are formed by the previously described structure of the flexible collar 82 including a top opening 104 bordered by the angled inner periphery of the transition wall 102 and a middle opening 106 bordered by the angled inner periphery of the flexible seal 84, the combination of which serve as a guide structure for insertion of a probe body, such as the probe body 24a, partially through the flexible collar 82. A capture annulus 108 is formed by the junction of the inside surface of the outer wall 94, the region underlying a portion of the top wall 100 and the inside surface of the bottom wall 98 for captured accommodation of the lip 34a of the immersion bag 16a and the capture ring 86 and O-ring 90. An expansive bottom opening 110 is provided generally extending between and bounded by the lower to mid-region of the capture annulus 108 and the bottom edge of the flexible seal 84 through which a portion of the nontapered body section 24c of the ultrasound probe 12a can maintain slideable sealed engagement with the flexible seal 84. One or more optional self-sealing valves 109 in tubular or cylindrical form or of other suitable structure are shown in dashed lines located along, about and extending through the transition wall 102 offering communication between ambient and the interior 32a of the immersion bag 16a.

Figure 18:
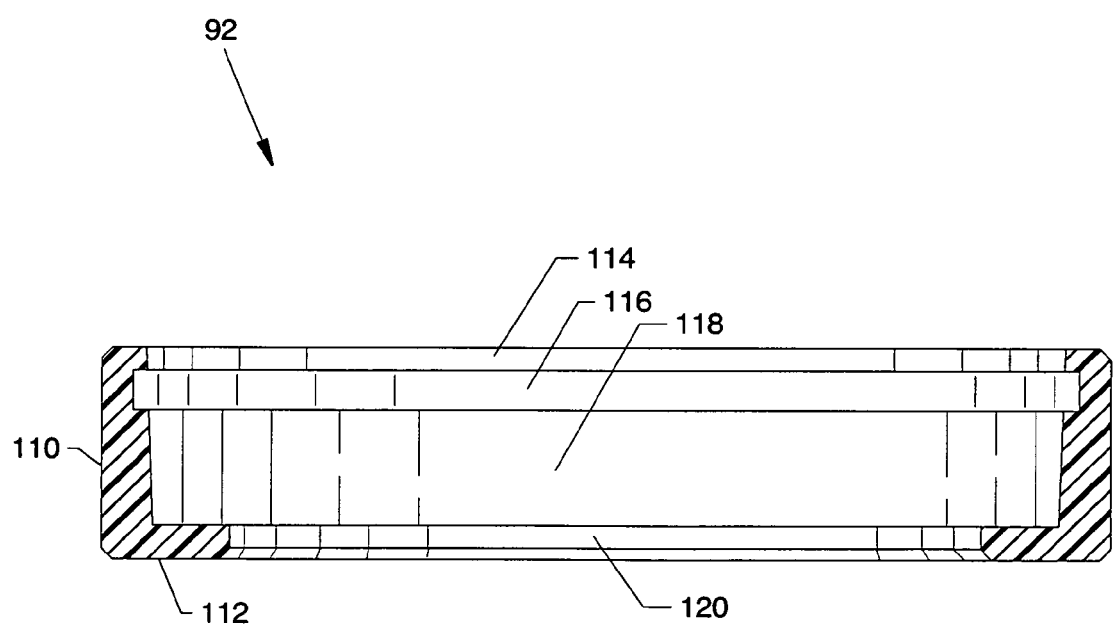
FIG. 18 is a cross section view of the one-piece maneuvering ring along line 18-18 of FIG. 15 in order to show the general structure of the maneuvering ring.

FIG. 18 is a cross section view of the one-piece maneuvering ring 92 along line 18-18 of FIG. 15 in order to show the general structure of the maneuvering ring 92. The maneuvering ring 92 frictionally engages over and about the combined structure of the flexible collar 82, the O-ring 90, the lip 34a of the immersion bag 16a, the immersion bag 16a, and the capture ring 86 as shown in FIG. 21. The use of the maneuvering ring 92 supplies a structure having a measured amount of rigidity in order that the user can grasp and position the immersion bag 16b with respect to the eye or other surface being examined without the danger of disturbing the integrity of the probe/seal valve 49b. The interior geometry of the maneuvering ring 92 snappingly engages the exterior geometry of the flexible collar 82 in mutual coaxial engagement to secure about the capture ring 86, the lip 34a of the immersion bag 16a, and the O-ring 90. The maneuvering ring 92 includes an annular outer wall 111, a bottom wall 112 which intersects and extends inwardly a short distance from the bottom of the outer wall 111, a top opening 114, an annular receptor groove 116 adjacent the top opening 114 recessingly extending into the inner surface of the outer wall 111, a middle opening 118 adjacent and below the receptor groove 116, and a beveled bottom opening 120 located below and adjacent the middle opening 118 and between the inner edge of the bottom wall 112. The receptor groove 116 of the maneuvering ring 92 snappingly engages the annular ring 96 extending from the flexible collar 82 as the flexible collar 82 gains entry through and into the structure of the maneuvering ring 92, first by entering the top opening 114 followed by entry adjacent the annular receptor groove 116 and finally into the middle opening 118 where resistance to further positioning is subsequently offered by contact with the bottom wall 112.

Figure 19:
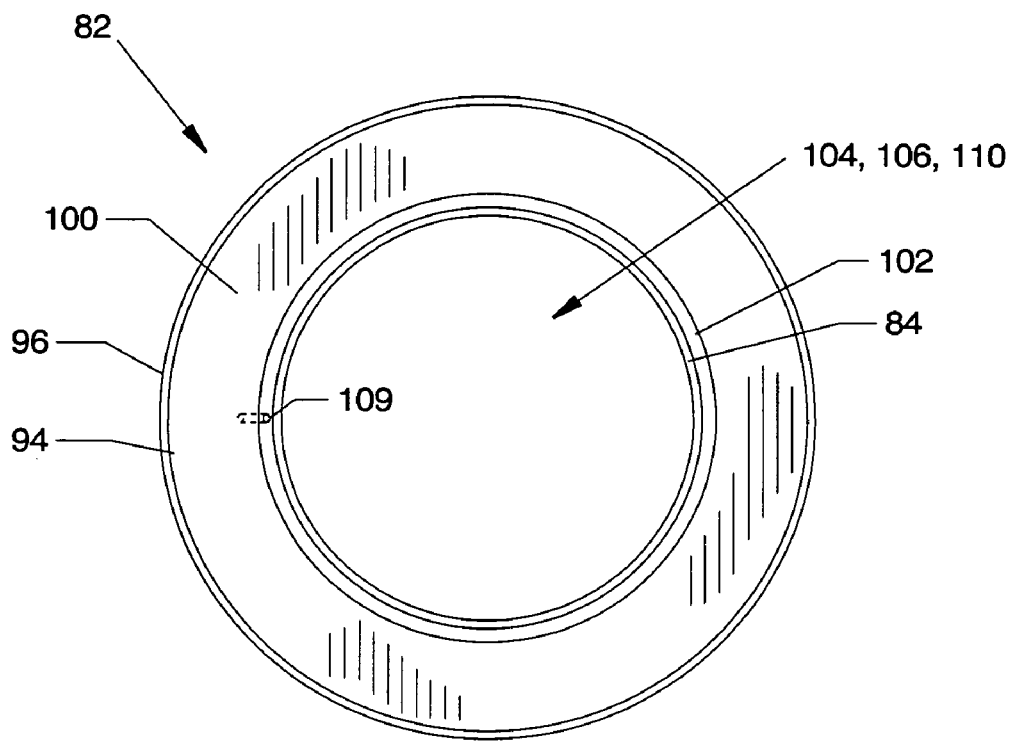
FIGS. 19 and 20 are top and bottom views respectively of the flexible collar including the flexible seal.
Figure 20:
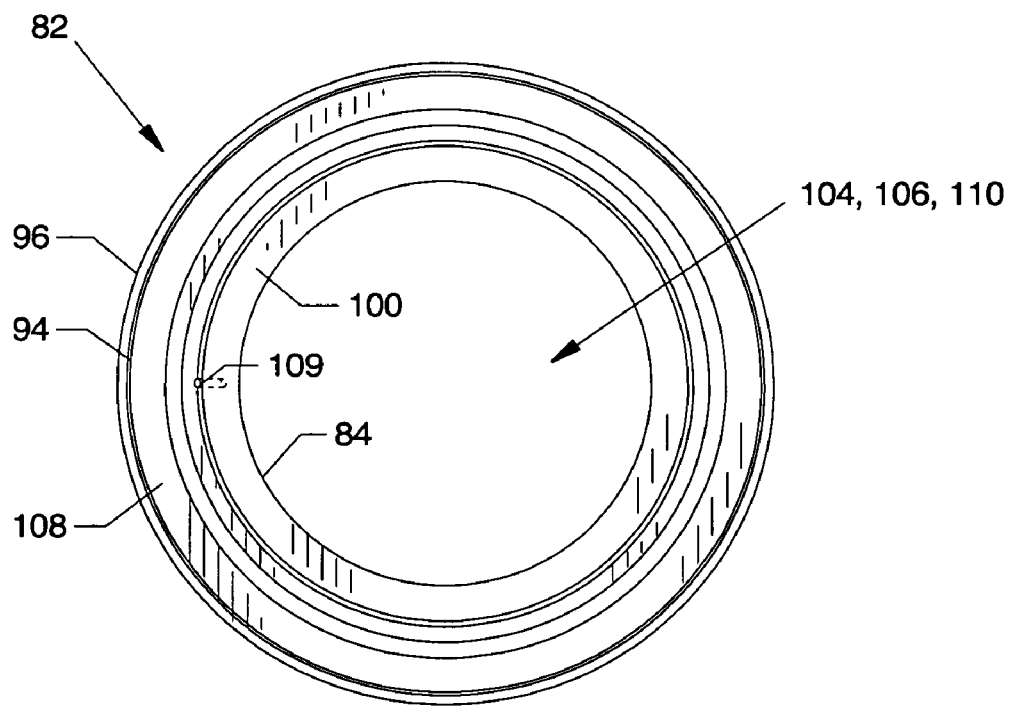

FIGS. 19 and 20 are top and bottom views, respectively, of the flexible collar 82, including the flexible seal 84. Also shown is one optional self-sealing valve 109 extending through the transition wall 102 of the flexible collar 82 and other annular structure of the flexible collar 82. The use of one or more optional self-sealing valves 109 can be utilized to vent the interior 32a of the immersion bag 16a when the tip of the ultrasound probe 12a is introduced into the interior 32a of the immersion bag 16a. Air, gas, liquids, gels, or other mediums or fluids can be displaced or vented through the optional self-sealing valve(s) 109 during introduction of the tip of the ultrasound probe 12a or during further operation of the invention. The size of the optional self-sealing valve(s) 109 is shown in exaggerated form for purposes of illustration. In actual practice, the choice of including optional self-sealing valve(s) 109 or of self-sealing valves 50a-50n which alternatively can be in the form of narrow gaps, slits or of related shape decreasing geometry structure or other suitable structure, are parted by the force of the expelled or displaced air, gas, liquid, aqueous mediums, gel, or the like, and modulate toward or to a closed state upon equalization between the interior 32a of the immersion bag 16a and ambient pressure. The self-sealing valve(s) 109 could be of different sized similar structure to operate across a pressure relief range. The purpose of the structure of the optional/additional self-sealing valve(s) 109 or optional/additional self-sealing valves 50a-50n is to prevent breakage of the immersion bag 16a by displacing air and to act as a fluid overflow. The optional self-sealing valve(s) 109 can ensure adequate hydraulic force to remove wrinkles, if any, in the immersion bag 16a, which result in acoustic artifacts (typically, arcuate shaped noise above the examining surface). Such hydraulic force also provides resistance so that the ultrasound probe 12a is prevented from coming into direct or indirect contact with the cornea of the eye.

FIG. 21 is a partial cross section view showing engagement of the immersion bag 16a of the immersion bag system 10b by the tip of the ultrasound probe 12a, i.e., the nontapered body section 24c. The immersion bag system 10b shown includes the flexible collar 82, including the flexible seal 84, the capture ring 86, and the immersion bag 16a fully arranged and assembled using the structural features of such components in suitable engagement made possible by the elastic qualities of the involved components in combination with the fixation of the lip 34a and the juxtaposed upper portion of the immersion bag 16a within the capture annulus 108 by frictional engagement between the capture annulus 108 and the capture ring 86. Other additional fixation and securing methods can be used in addition, such as, but not limited to, the use of heat staking, adhesive, or other suitable attachment. Additionally, the lip 34a of the immersion bag 16a is sealingly held between the inner surface of the outer wall 94 of the flexible collar 82 by the forced positioning of and by the forced engagement of the capture ring 86 against the lip 34a in cooperation with the spongy and elastic qualities of the flexible collar 82. The flexible seal 84 flexes to sealingly accommodate and frictionally engage and seal against the nontapered body section 24c of the ultrasound probe 12a in the formation of the probe/seal valve 49b. The tip of the ultrasound probe 12a is positioned within the interior 32a of the immersion bag 16a, wherein the transducer 26a is spaced sufficiently from the end 30a of immersion bag 16a to allow flexing of the end 30a in a spaced relationship with the eye and to prevent contact of the transducer 26a with the end 30a of immersion bag 16a during such flexing. The mode of operation of this second alternative embodiment is substantially the same as described for the immersion bag system 10a, the difference being that the flexible collar 82 is substituted for the flexible collar 62, the shape of the immersion bag 16a is substantially conical with an arcuate end 30a and the maneuvering ring 92 is included. In this embodiment, the general shape of the immersion bag 16a is a combination of a conical shape terminating in an arcuate shape, whereby such a combination provides a minimum, i.e., not an excessive amount of material at the site of contact with the cornea, thereby minimizing bunching or folding of the immersion bag 16a. The arcuate shape of the end 30a reverses upon contact with the cornea 56 to conformingly drape about the shape of the cornea in one-to-one correlation. Although the flexible collar 82 has been characterized as being an alternative to the flexible collars 18 and 62, neither collar is to be construed as being preferred over the other, each having equal stature.

Figure 22:
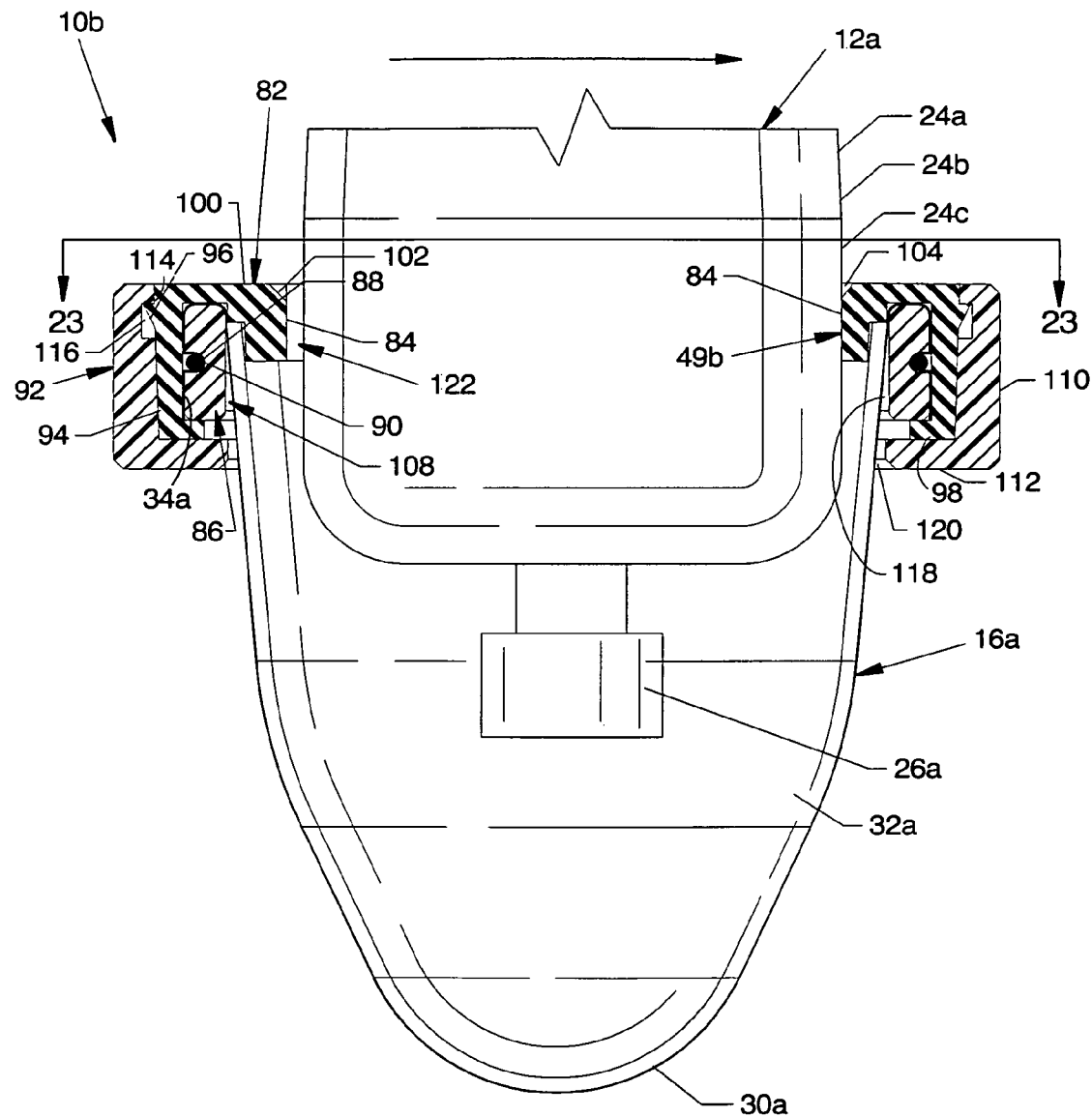
FIG. 22 is a view like FIG. 21 where sideways force is exerted upon the ultrasound probe thereby urging the ultrasound probe off center with respect to the flexible seal.

FIG. 22 is a view like FIG. 21 where sideways force is exerted upon the ultrasound probe 12a, thereby urging the ultrasound probe 12a off center with respect to the flexible seal 84 of the flexible collar 82 to create a gap 122 between the flexible seal 84 and the nontapered section 24c of the ultrasound probe 12a, thus opening the probe/seal valve 49b to allow transfer of air or aqueous medium through the gap 122. The geometry of the probe/seal valve 49b is influenced by this action to open the probe/seal valve 49b. The geometry of the probe/seal valve 49b can be otherwise influenced by angulating or rocking the ultrasound probe 12a to cause deformation of and opening of the probe/seal valve 49b by creating other gap(s) to allow transfer of air or aqueous medium through such gap(s). The flexible qualities of the flexible seal 84 accommodate such movement of the ultrasound probe 12a.

Figure 23:
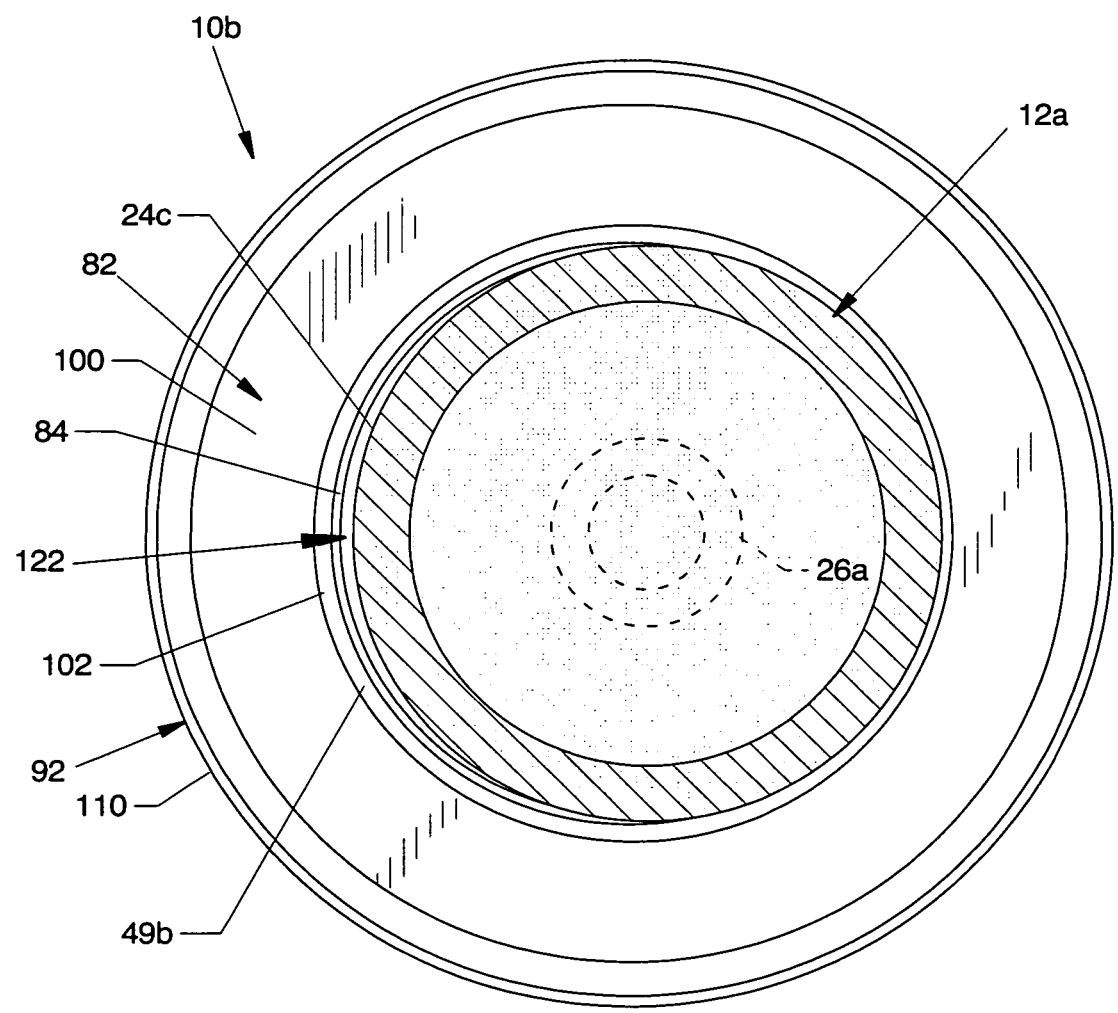
FIG. 23 is a top view in partial cross section along line 23-23 of FIG. 22 showing the off-center location of the ultrasound probe and the gap created by the deforming of the annular sealing aspect of the probe/seal valve to open the probe/seal valve.

FIG. 23 is a top view in partial cross section along line 23-23 of FIG. 22 showing the off-center location of the ultrasound probe 12a and the gap 122 created by the deforming of the annular sealing aspect of the probe/seal valve 49b to open the probe/seal valve 49b. Gaps are also created in the previous embodiments in the same manner as just described with reference to FIGS. 22 and 23.

Figure 24:
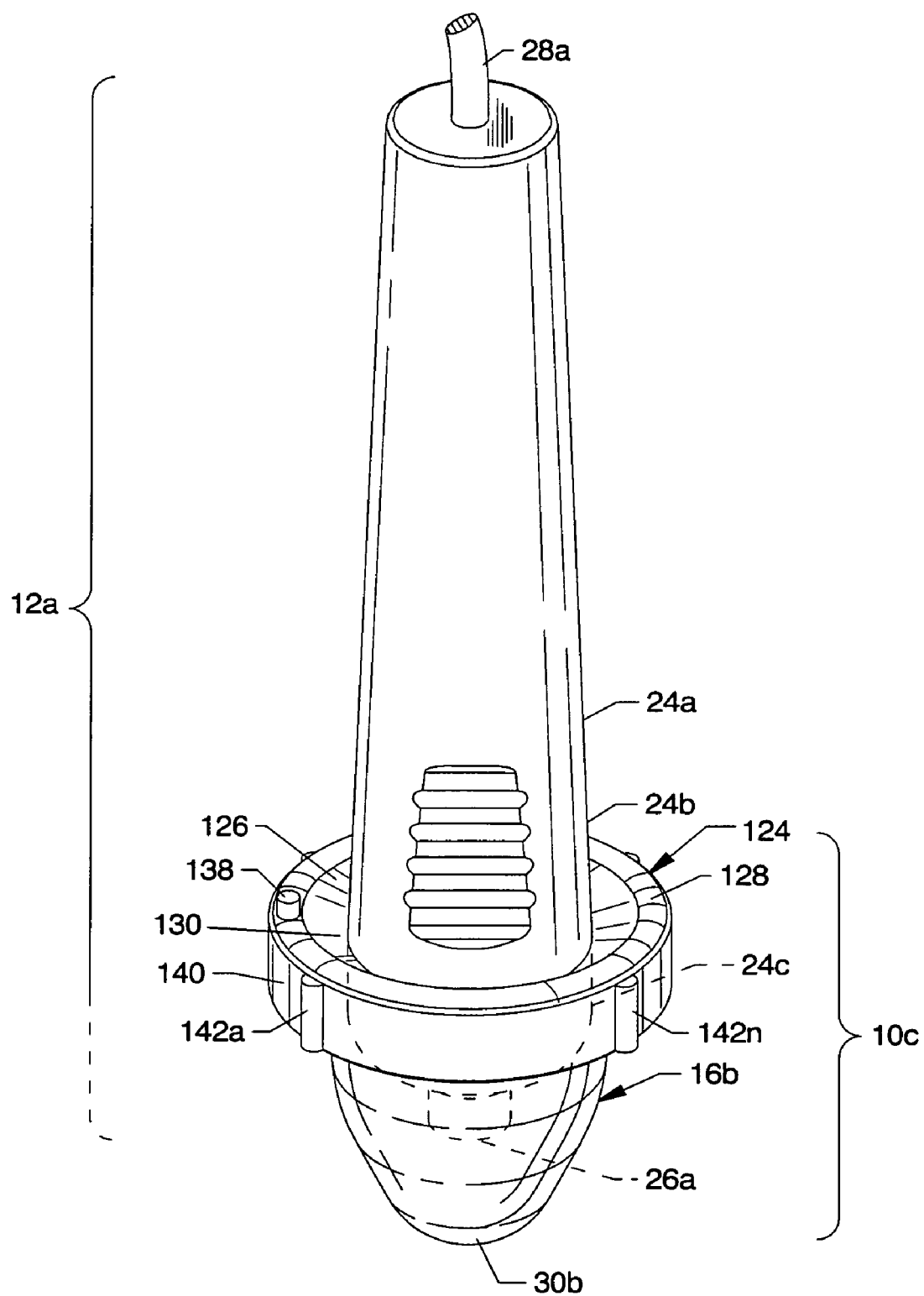
FIG. 24, an alternative embodiment, is an isometric view of an immersion bag system shown affixed to and in use with another form of the ultrasound probe.
Figure 26:
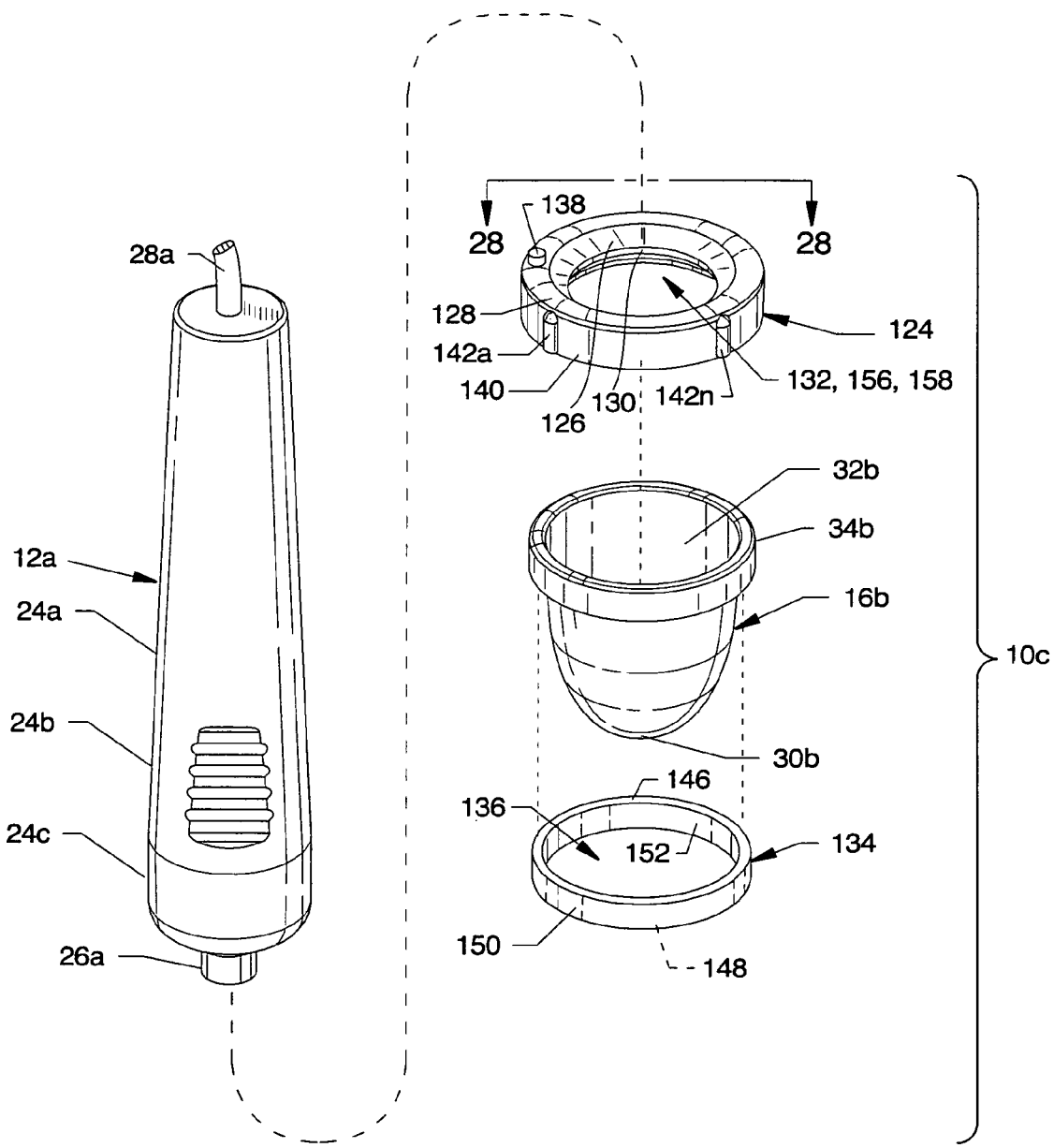
FIG. 26 is an exploded isometric top view of the immersion bag system shown distanced from the ultrasound probe.
Figure 27:
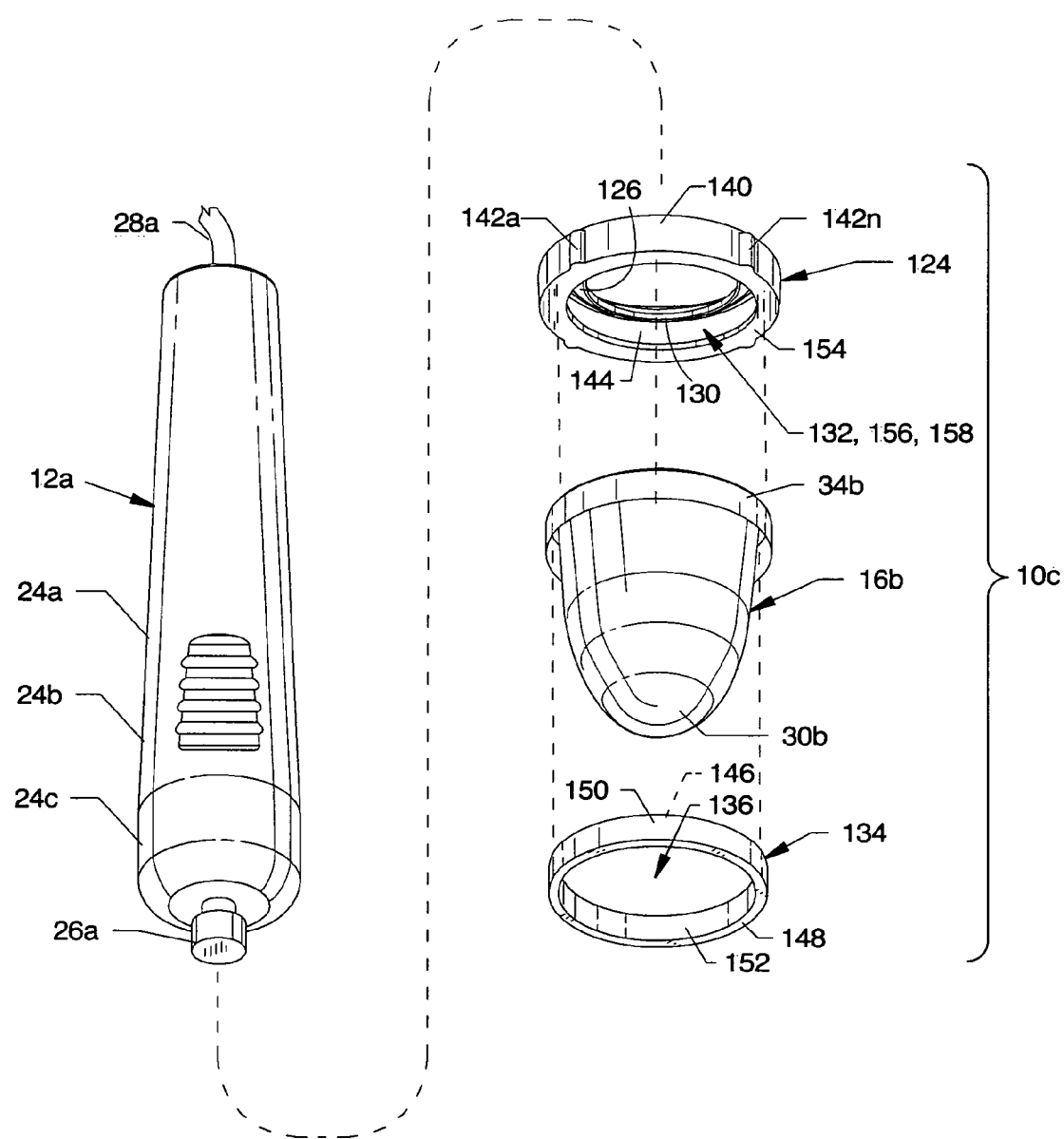
FIG. 27 is an exploded isometric bottom view of the immersion bag system shown distanced from the ultrasound probe.

FIG. 24 is an isometric view of an immersion bag system 10c, a third alternative embodiment, shown affixed to and in use with an ultrasound probe 12, herein designated as ultrasound probe 12a. The lower region of the ultrasound probe 12a is sealed in close association with the following components comprising the immersion bag system 10c each with flexible or semi-rigid qualities including: a flexible immersion bag 16b, a flexible collar 124 having a tapered integral flexible seal 126 extending inwardly and at a downward angle from a curved top wall 128 which has an inwardly facing wall annular sealing edge 130 defining a middle opening 156 (FIG. 25), and a capture ring 134 which can be semi-rigid having an opening 136, each of which is shown in FIGS. 25, 26 and 27.

The upper peripheral portion of the flexible collar 124 includes an upwardly extending ultrasound transducer wave direction reference protrusion 138 useful for indexing the mutual positioning of the combined ultrasound probe 12a and the flexible collar 124 in order to maintain reference and to properly guide the ultrasonic output of the ultrasonic probe 12a. The periphery of the outer wall 140 of the flexible collar 124 includes a plurality of vertically aligned bars 142a-142n. The bars 142a-142n minimize or prevent inadvertent rolling of the immersion system 10c and an engaged ultrasound probe 12a along and from a flat surface, such as a table top or other flat resting surface, onto the floor, thus preventing damage to the ultrasound probe 12a.

The lower region of the ultrasound probe 12a is also closely associated with the components of the immersion bag system 10c including the annular sealing edge 130 of the flexible collar 124 and the interior of the immersion bag 16b. The body 24a of the ultrasound probe 12a is, for the most part, a tapered tubular structure including tapered body section 24b and a nontapered body section 24c, and includes a transducer 26a at one end and also houses other internal components associated with the operation of the transducer 26a. A control/power cable 28a exits from one end of the ultrasound probe 12a for connection to external support components associated with operation of the transducer 26a.

Figure 25:
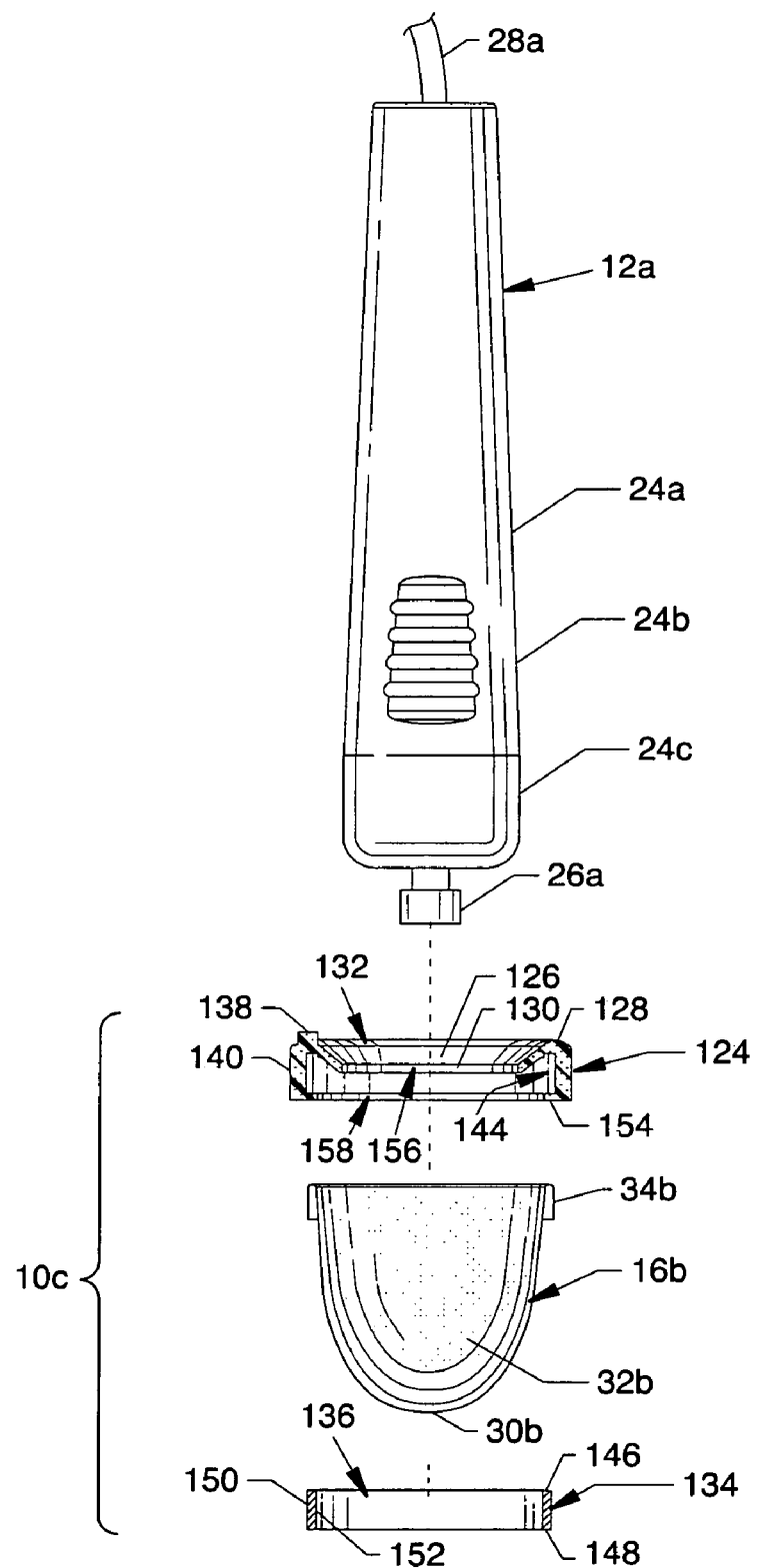
FIG. 25 is a partially exploded view of the sterile immersion bag system incorporated to frictionally engage the lower nontapered portion of the ultrasound probe.

FIG. 25 is an exploded side view of the sterile immersion bag system 10c incorporated to frictionally engage the nontapered body section 24c of the ultrasound body 24a shown at the lower region of the ultrasound probe 12a. The structure of the immersion bag system 10c includes the flexible immersion bag 16b, the flexible collar 124 with the flexible seal 126 and annular sealing edge 130 integral to the flexible collar 124, and the capture ring 134 where the flexible collar 124, the flexible seal 126 and the capture ring 134 can be semi-rigid. The immersion bag system 10c provides features suitable for a sealed communication with a pressure relieving capability and/or maneuvering of the immersion bag system 10c with respect to the lower portion, i.e., the nontapered body section 24c of the ultrasound probe 12a.

The flexible seal 126, which is integral to and part of the flexible collar 124, is of a general annular shape, preferably being fashioned of a flexible material, such as silicone, but not limited thereto, but could be foam, preferably close cell foam, latex, rubber, plastic, or other suitable flexible and pliable material. The capture ring 134 is made of thick walled cardboard, preferably closed cell cardboard, paper or other suitable material, and includes annular and planar top and bottom surfaces 146 and 148, respectively. The capture ring 134 includes an outer annular surface 150 and an inner annular surface 152 extending between the top annular surface 146 and the bottom annular surface 148. Once engaged onto the nontapered body section 24c of the ultrasound probe 12a, the flexible seal 126 is watertight permitting examinations in any position (e.g., patient sitting upright or laying down).

The immersion bag 16b is formed of a thin and flexible pliable acoustically invisible material (for example and demonstration, in a range of 0.1 micron to 250 microns), such as polyethylene, hydrophilic plastic or other suitable material which is capable of containing a gel or other suitable medium and which allows the passage of ultrasound waves. The immersion bag 16b preferably is substantially a conical shape for the greatest portion thereof and includes an end 30b which is arcuate in profile and also includes an interior 32b. The top of the immersion bag 16b is reversed a short distance outwardly and about itself to form a lip 34b of annular shape extending about the upper region of the immersion bag 16b for accommodation of the capture ring 134. The lip 34b is shown substantially as it would subsequently appear when forced and depressed into an inwardly facing truncated capture annulus 144 located at the interior of the flexible collar 124 by the capture ring 134, such as when securing the lip 34b of the immersion bag 16b to the flexible collar 124.

FIG. 26 is an exploded isometric top view of the immersion bag system 10c shown distanced from the ultrasound probe 12a, and FIG. 27 is an exploded isometric bottom view of the immersion bag system 10c shown distanced from the ultrasound probe 12a. An annular and planar bottom wall 154 (FIG. 27), which is integral to and being a feature of the flexible collar 124, is shown extending inwardly from the lower region of the outer wall 140 of the flexible collar 124 to form a portion of the capture annulus 144. The structure of the flexible collar is further described and shown in FIG. 28.

Figure 28:
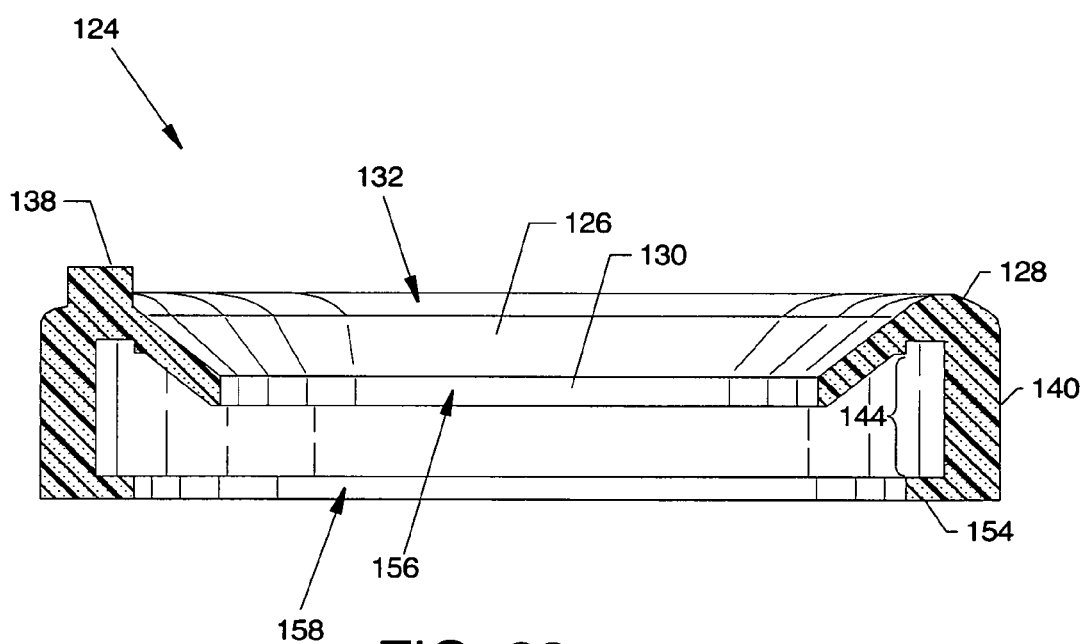
FIG. 28 is a cross section view of the one-piece flexible collar shown in FIGS. 26 and 27 along line 28-28 of FIG. 26 in order to show the general structure of the flexible collar.
Figure 31:
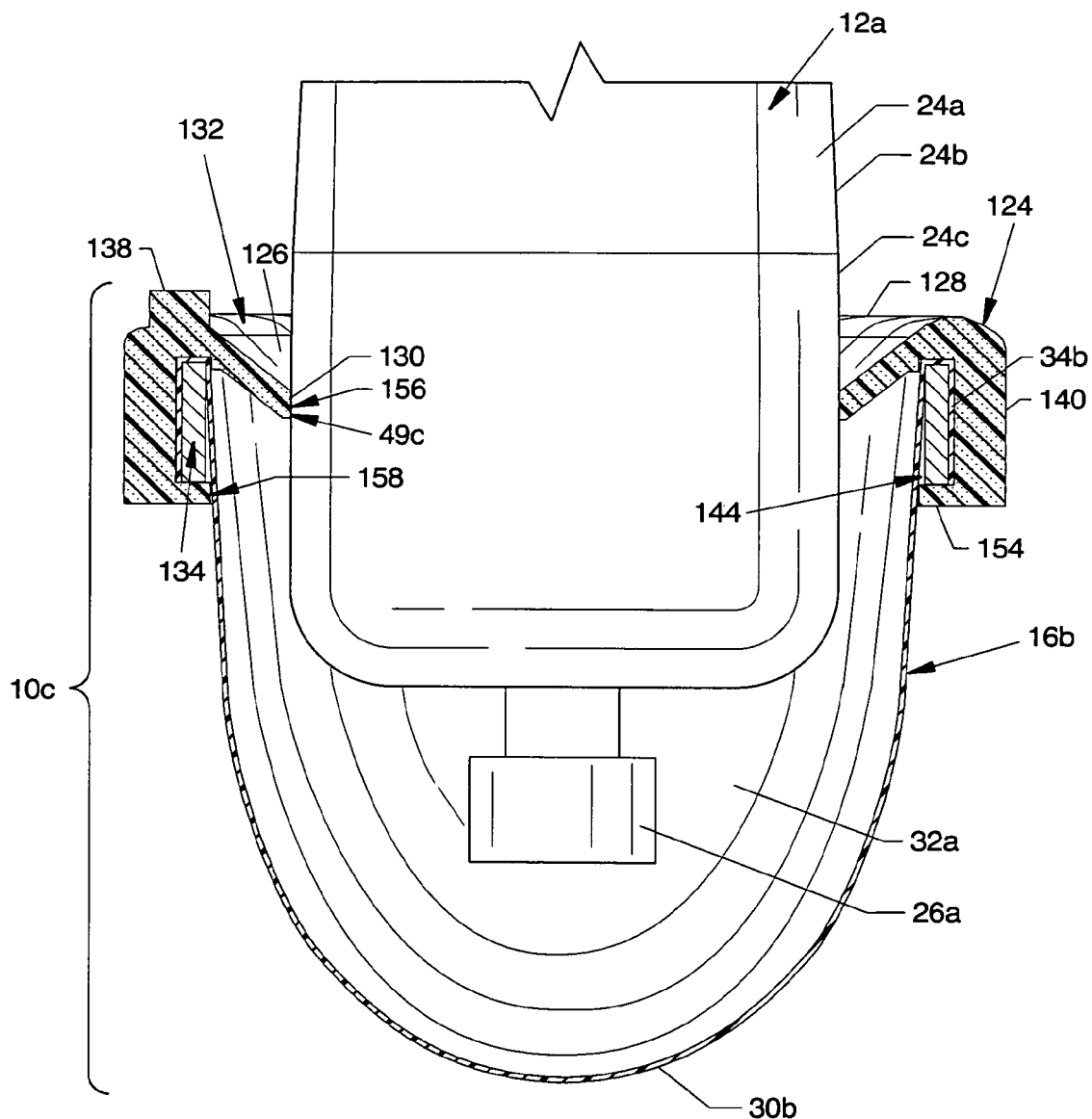
FIG. 31 is a partial cross section view showing engagement of the immersion bag system by the tip of the ultrasound probe.

FIG. 28 is a cross section view of the one-piece flexible collar 124, also shown in FIGS. 26 and 27, taken along line 28-28 of FIG. 26, in order to show the general structure of the flexible collar 124. The continuously formed flexible collar 124 is comprised of a plurality of geometrically configured and connecting structures including the vertically oriented outer wall 140, the horizontally oriented bottom wall 154 which is annular and which intersects the lower region of the outer wall 140 and extends inwardly a short distance therefrom and forming the bottom opening 158, a horizontally oriented curved profile top wall 128 which intersects the upper region of the outer wall 140, the angled flexible seal 126 extending inwardly and downwardly at an angle from the top wall 128, and the annular sealing edge 130 at the lower region of the flexible seal 126. The annular sealing edge 130 at the lower portion of the flexible seal 126 is brought into flexed contact with the nontapered body section 24c of the ultrasound probe 12a. Such an arrangement and relationship of the ultrasound probe 12a with the flexible seal 126 results in formation of an annular shaped deformable probe/seal valve 49c which is formed as shown in FIG. 31, whereby such an arrangement and relationship is perfected by the engagement of the nontapered body section 24c of the body 24a of the ultrasound probe 12a with the annular sealing edge 130 of the flexible seal 126. Other annular open regions are formed by the previously described structure of the flexible collar 124 including a top opening 132 bordered by the top wall 128, the middle opening 156 bordered by the annular sealing edge 130 of the flexible seal 126, the combination and use of which serve as a guide structure for insertion of a probe body, such as the probe body 24a, partially through the flexible collar 124. A bottom opening 158 for accommodation of the ultrasound probe 12a, the immersion bag 16b and the capture ring 134 is provided by the inner periphery of the bottom wall 154. The capture annulus 144 is formed by the junction of the inside surface of the outer wall 140, the region underlying a portion of the top wall 128 and the inside upper surface of the bottom wall 154 for the captured accommodation of the lip 34b of the immersion bag 16b and the capture ring 134.

Figure 29:
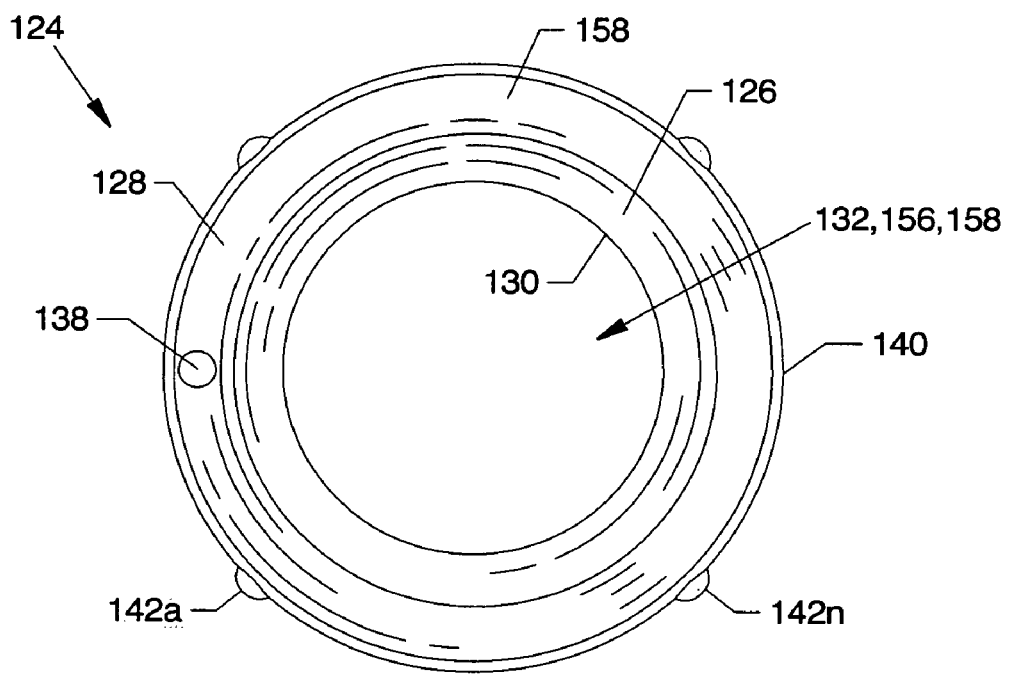
FIGS. 29 and 30 are top and bottom views respectively of the flexible collar including the flexible seal.
Figure 30:
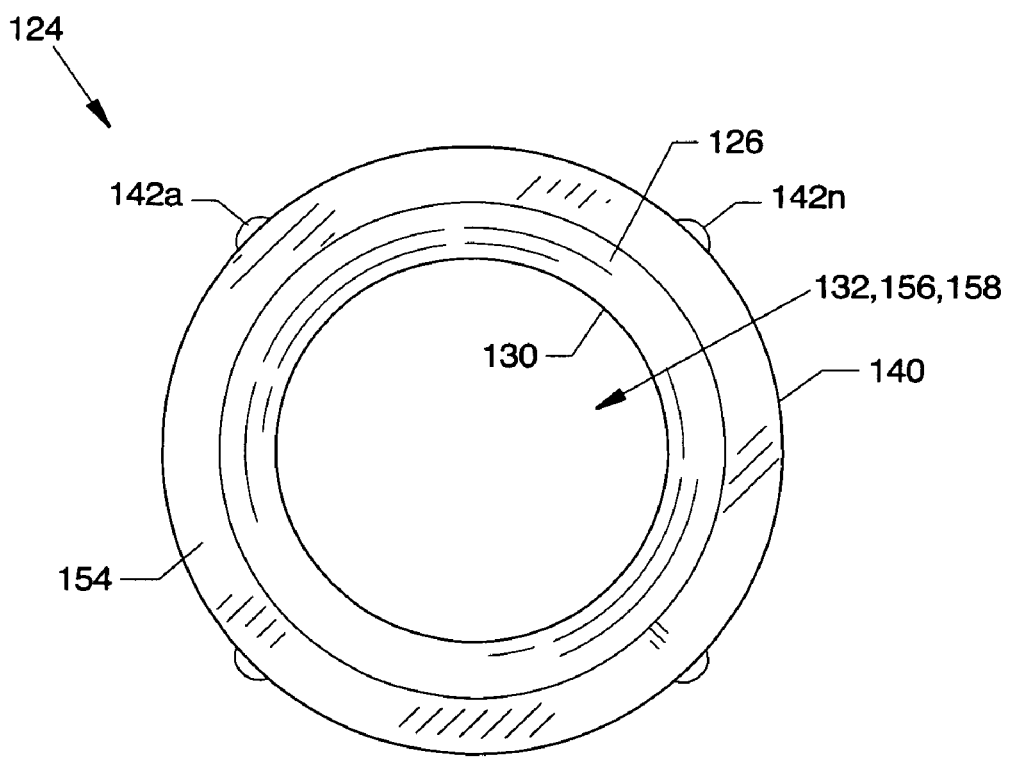

FIGS. 29 and 30 are top and bottom views, respectively, of the flexible collar 124, including the flexible seal 126.

FIG. 31 is a partial cross section view showing the engagement of the immersion bag 16b of the immersion bag system 10c by the tip of the ultrasound probe 12a, i.e., the nontapered body section 24c. The immersion bag system 10c shown includes the flexible collar 124, including the flexible seal 126, the capture ring 134, and the immersion bag 16b fully arranged and assembled using the structural features of such components in suitable engagement made possible by the elastic qualities of the involved components in combination with the fixation of the lip 34b and the juxtaposed upper portion of the immersion bag 16b within the capture annulus 144 by frictional engagement between the capture annulus 144 and the capture ring 134. Other additional fixation and securing methods can be used in addition, such as, but not limited to, the use of heat staking, adhesive, or other suitable attachment methods, as described in a previous embodiment. Additionally, the lip 34b of the immersion bag 16b is sealingly held between the inner surface of the outer wall 140 of the flexible collar 124 by the forced positioning of and by the forced engagement of the capture ring 134 against the lip 34b in cooperation with the spongy and elastic qualities of the flexible collar 124, whereby the lip 34b is secured within the capture annulus 144. The flexible seal 126 flexes to sealingly accommodate and frictionally engage and seal against the nontapered body section 24c of the ultrasound probe 12a in the formation of the probe/seal valve 49c having annular qualities extending along and about an annular region of contact between the annular sealing edge 130 and the circumferential outer surface of the nontapered body section 24c. The tip of the ultrasound probe 12a is positioned within the interior 32b of the immersion bag 16b, wherein the transducer 26a is spaced sufficiently from the end 30b of immersion bag 16b to allow flexing of the end 30b in a spaced relationship with the eye and to prevent contact of the transducer 26a with the end 30b of the immersion bag 16b during such flexing. The general mode of operation of this third alternative embodiment is substantially the same as described for the immersion bag system 10a, the difference being that some complex components are eliminated and other components are substituted to provide for an economy of components and simpler components and assemblies which subsequently provide the same or improved results with the same benefit to the patient's eyes. In this embodiment, the general shape of the immersion bag 16b is a combination of a conical shape terminating in an arcuate shape, whereby such a combination provides a minimum, i.e., not an excessive amount of material at the site of contact with the cornea, thereby minimizing bunching or folding of the immersion bag 16b. The unique conical shape of the immersion bag 16b and others allows the physician to more accurately position the immersion bag 16b on the desired position on the eye. The arcuate shape of the end 30b reverses upon contact with the cornea 56 to conformingly drape about the shape of the cornea in one-to-one correlation. Although the flexible collar 124 has been characterized as being an alternative to the flexible collars 18 and 62 and 82, none of the collar is to be construed as being preferred over the others, each having equal stature.

The use of the previously and further described probe/seal valve 49c can be utilized to vent the interior 32b of the immersion bag 16b when the tip of the ultrasound probe 12a is introduced into the interior 32b of the immersion bag 16b. Air, gas, liquids, gels, or other mediums or fluids can be displaced or vented through the self-sealing probe/seal valve 49c during introduction of the tip of the ultrasound probe 12a or during further operation of the invention by manually deforming the probe/seal valve 49c, as described later in detail. One purpose of the structure of the probe/seal valve 49c arrangement is to allow bag pressure modulation for examining eyes with low intraocular pressure by displacing air and to act as a fluid overflow. The probe/seal valve 49c can ensure adequate hydraulic force to remove wrinkles, if any, in the immersion bag 16b, which result in acoustic artifacts (typically, arcuate shaped noise above the examining surface). Such hydraulic force also provides resistance so that the ultrasound probe 12a is prevented from coming into direct or indirect contact with the cornea of the eye.

Figure 32:
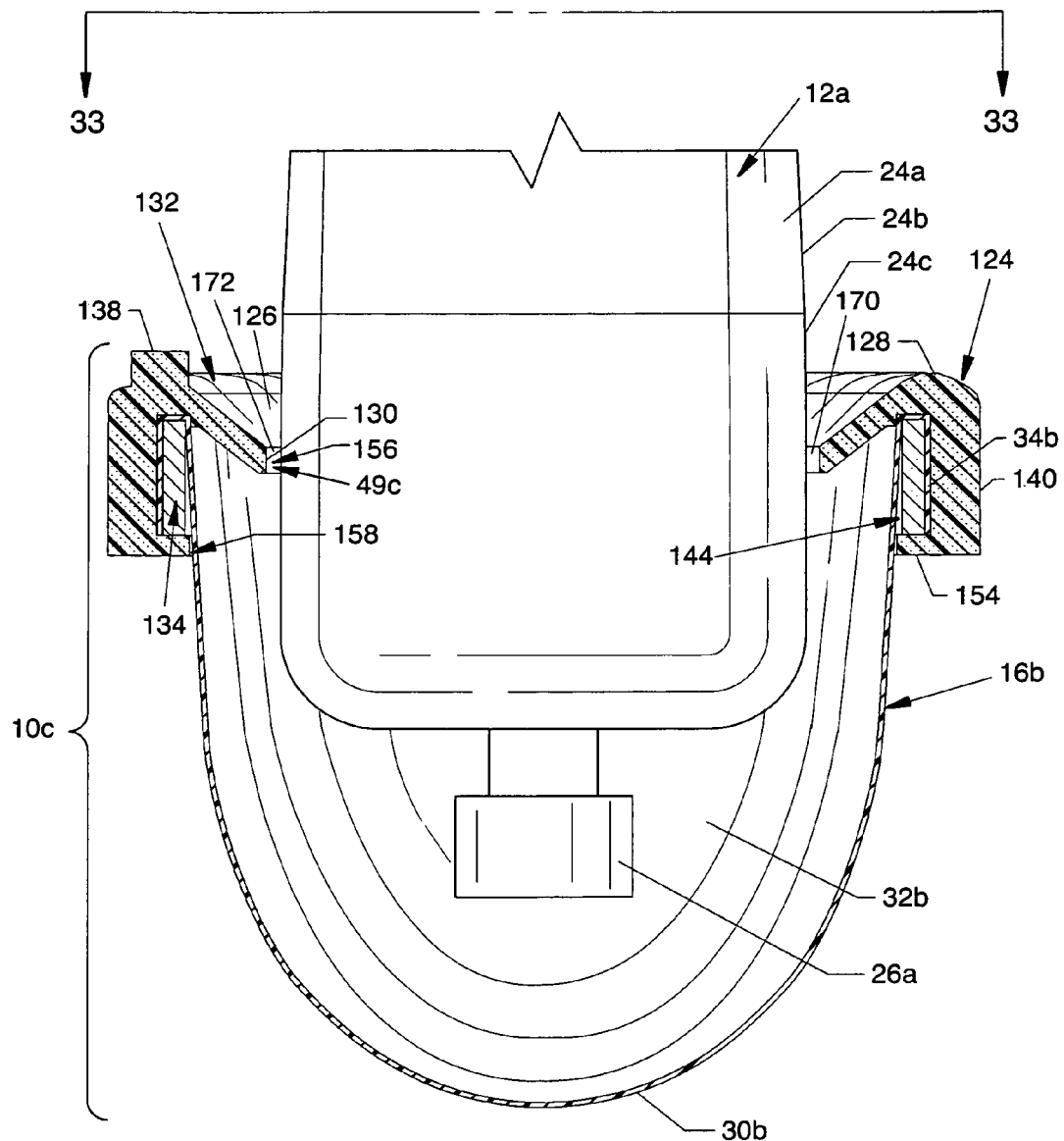
FIG. 32 is a view like FIG. 31 where sideways force is exerted upon the flexible collar and other components thereby urging the probe/seal valve to open; and, FIG. 33 is a top view in partial cross section along line 33-33 of FIG. 32 showing the opening of the probe/seal valve to temporarily form the gaps created by the deforming of the flexible collar and capture ring.
Figure 33:
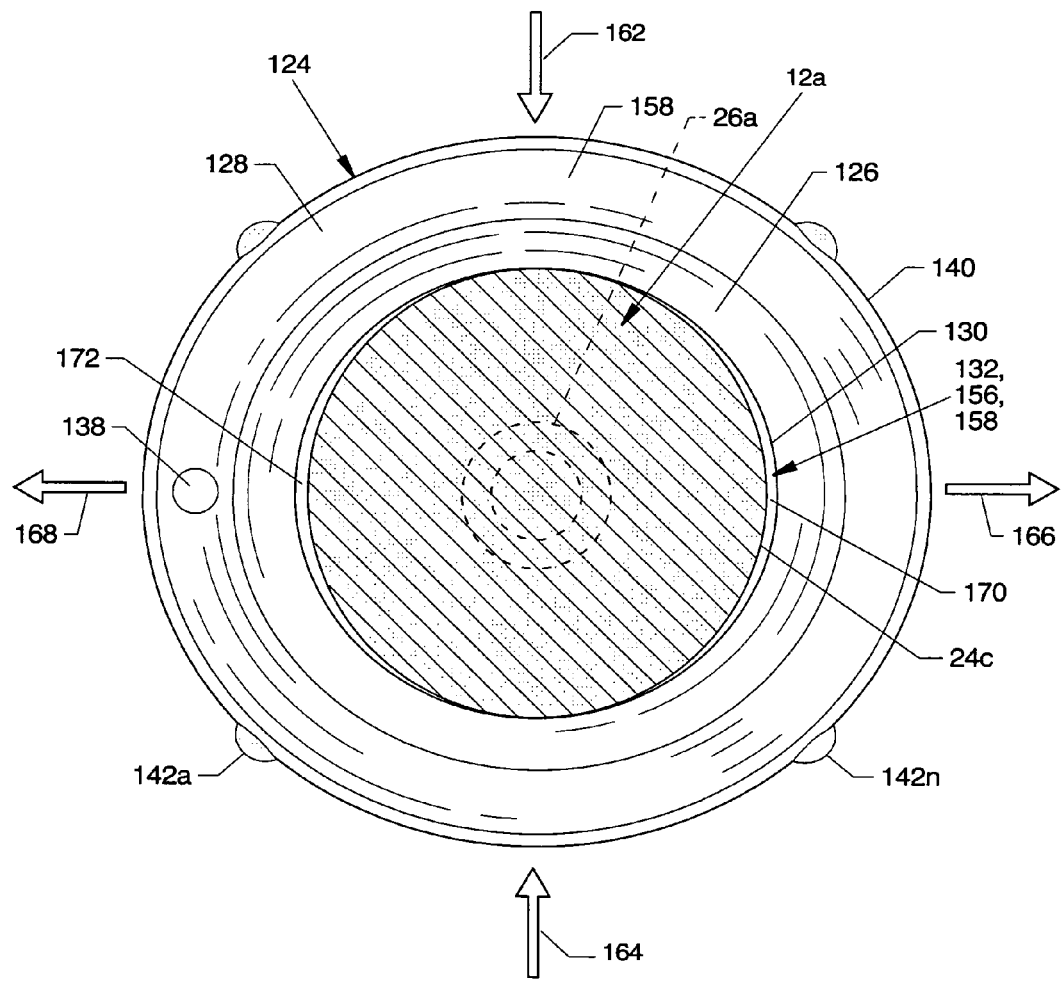

FIG. 32 is a view similar to FIG. 31, and FIG. 33 is a top view in partial cross section along line 33-33 of FIG. 32, where an inward exerted force is exerted by the physician at opposing side regions of the outer wall 140. For example, manual force can be applied to the outer wall 140 at a location as represented by applied force reference arrows 162 and 164 (FIG. 33) resulting in a temporarily inward reshaping of the flexible collar 124, the capture ring 134, the lip 34b, and the upper portion of the immersion bag 16b about the profile of the nontapered portion 24c of the ultrasound probe 12a, thus causing an outward expansion of the flexible collar 124, the capture ring 134, the lip 34b, and the upper portion of the immersion bag 16b, generally in the direction of the resultant movement reference arrows 166 and 168. Such action also temporarily reshapes the annular sealing edge 130 of the flexible collar 124 in the direction indicated by the resultant movement reference arrows 166 and 168, thereby causing areas of discontinuous contact, herein referred to as gaps 170 and 172, between the annular sealing edge 130 and the nontapered body section 24c of the ultrasound probe 12a to open the probe/seal valve 49c. Such described action allows transfer of air or aqueous medium through the gaps 170 and 172. Such influencing of the geometry of the probe/seal valve 49c causes the deformation of and opening of the probe/seal valve 49c thus allowing for the transfer of air or aqueous medium outwardly through the gaps 170 and 172 Relaxing and removal of the force at the region of the applied force reference arrows 162 and 164 causes the elastic memory of the flexible collar 124 to close and eliminate the gaps 170 and 172, thereby perfecting the seal of the annular sealing edge 130 of the flexible seal 126 against the nontapered section 24c of the ultrasound probe 12a.

Various modifications can be made to the present invention without departing from the apparent scope thereof.

PARTS LIST immersion bag system
10a immersion bag system
10b immersion bag system
10c immersion bag system
12 ultrasound probe
12a ultrasound probe
16 immersion bag
16a immersion bag (conical)
16b immersion bag
18 flexible collar
20 flexible seal
22 capture ring
24 body
24a body
24b tapered body section
24c nontapered body section
26 transducer
26a transducer
28 control/power cable
28a control/power cable
30 end
30a end
30b end
32 interior
32a interior
32b interior
34 lip
34a lip
34b lip
36 outer wall
38 top wall
40 transition wall 42 top opening
44 middle opening
46 capture annulus
48 bottom opening
49 probe/seal valve
49a probe/seal valve
49b probe/seal valve
49c probe/seal valve
50a-n self-sealing valves
52 opening
54 slit
56 cornea
58 eye
60 gel
62 flexible collar
63 flexible seal
64 outer wall
66 top wall
68 inner wall
70 angled transition wall
72 flexible seal
74 top opening
76 bottom opening
78 capture annulus
80a-n self-sealing valves
82 flexible collar
84 flexible seal
86 capture ring
88 annular groove
89 opening
90 O-ring
92 maneuvering ring
93 annular depression
94 outer wall
96 annular ring
98 bottom wall
100 top wall
102 transition wall
104 top opening
106 middle opening
108 capture annulus
109 self sealing valve
110 bottom opening
111 outer wall
112 bottom wall
114 top opening
116 receptor groove
118 middle opening
120 bottom opening
122 gap
124 flexible collar
126 flexible seal
128 top wall
130 annular sealing edge
132 top opening
134 capture ring
136 opening
138 ultrasound transducer wave direction reference protrusion
140 outer wall
142a-n bars
144 capture annulus
146 top annular surface
148 bottom annular surface
150 outer annular surface
152 inner annular surface
154 bottom wall
156 middle opening
158 bottom opening
162 applied force reference arrow
164 applied force reference arrow
166 resultant movement reference arrow
168 resultant movement reference arrow
170 gap
172 gap

The invention claimed is:

1. An immersion bag system for use with an ultrasound probe to overcome near field artifact comprising:
   a. a flexible thin wall thickness immersion bag with an attached flexible collar having an integral internal seal;
   b. the immersion bag having an upper open end and a closed lower end and further having an attached flexible collar with an integral annular internal seal for sealing about the upper open end and a tip portion of an ultrasound probe, the integral annular internal seal having at least one self-sealing valve extending along, about and through the annular internal seal thereby providing a unidirectional air passage after the tip portion of the ultrasound probe is in place, thereby providing for the escape of air or liquid from within the immersion bag to limit the pressure therein and close upon partial or complete equalization between the immersion bag interior and ambient pressure;
   c. the immersion bag is able to conform to a cornea, as well as to other surfaces, whether flat or irregular, thereby enabling an ultrasound probe to be used easily on such surfaces; and,
   d. the ultrasound probe, in use with the immersion bag system, is maintained at a distance above the contact surface of the immersion bag and is positionable about the vertical axis while the immersion bag maintains stationary conformal contact with the structure against which it is in contact.

2. An immersion bag system for use with an ultrasound probe to overcome near field artifact of a surface of an object to be ultrasonically examined, the immersion bag system comprising:
   a. a flexible thin wall thickness immersion bag, the flexible thin wall thickness immersion bag having a substantially conical shape, with an arcuate lower end and a top reversed outwardly upon itself, the flexible thin wall immersion bag containing an ultrasound transmission medium;
   b. the immersion bag having an upper open end and a closed lower end and further having an attached flexible collar with an integral annular internal seal for sealing about the upper open end and a tip portion of an ultrasound probe, the integral annular internal seal having at least one self-sealing valve extending along, about and through the annular internal seal thereby providing a unidirectional air passage after the tip portion of the ultrasound probe is in place, thereby providing for the escape of air or liquid from within the immersion bag to limit the pressure therein and close upon partial or complete equalization between the immersion bag interior and ambient pressure;
   c. the flexible collar, the flexible collar having an upward extending ultrasound transducer wave direction reference protrusion, an outer wall, the outer wall including a plurality of bars about the periphery in alignment with the collar to minimize rolling when on a flat resting surface, and a capture annulus formed and defined between the outer wall and the upward extending ultrasound transducer wave direction reference protrusion;

d. a capture ring for capturing the top reversed outwardly upon itself of the flexible thin wall immersion bag within the capture annulus of the flexible collar, with the top reversed outwardly upon itself at least partially encircling the capture ring and the top reversed upon itself at least partially encircled by the capture annulus; and, e. wherein, when the ultrasound probe is sealed in close association with the immersion bag system and prepared for use with the immersion bag in conforming contact with a surface to be ultrasonically probed, the tip end of the ultrasound probe is maintained at a distance above the surface of the immersion bag opposite of where the bag is in conforming contact with the surface of the object to be ultrasonically probed and the tip end of the ultrasonic probe is positionable about a vertical axis of the immersion bag system while the immersion bag maintains stationary conformal contact with the surface of the structure to be ultrasonically examined and against which the ultrasonic immersion bag system is in contact.

3. The immersion bag system of claim 2, wherein the object to be ultrasonically examined is a anterior ocular structure.

4. The immersion bag system of claim 3, wherein the anterior ocular structure to be examined is a cornea.

5. The immersion bag system of claim 2, wherein the immersion bag is formed of an acoustically invisible material.

6. The immersion bag system of claim 5, wherein the acoustically invisible material is selected from the group consisting of polyethylene and hydrophilic plastic.

7. The immersion bag system of claim 2, wherein the outer wall of the flexible collar further includes a horizontally oriented bottom wall extending inwardly a short distance from the outer wall, which bottom wall prevents the capture ring from exiting the capture annulus.

8. An ultrasound probe comprising an elongated rigid body and an immersion bag system, said elongated rigid body having a distal end and a proximal end, said distal end having a substantially cylindrical section, a power/cable attached to and extending externally from said proximal end, an ultrasound transducer attached to said distal end, an immersion bag system including an immersion bag having an upper open end and a closed lower end and further having an attached flexible collar with an integral annular internal seal for sealing about the upper open end and a tip portion of an ultrasound probe, the integral annular internal seal having at least one self-sealing valve extending along, about and through the annular internal seal thereby providing a unidirectional air passage after the tip portion of the ultrasound probe is in place, thereby providing for the escape of air or liquid from within the immersion bag to limit the pressure therein and close upon partial or complete equalization between the immersion bag interior and ambient pressure.

9. The ultrasound probe of claim 8, wherein said immersion bag has a substantially conical shape with a reversed end forming an outer lip at an open end of said immersion bag, a capture ring surrounding said open end of said immersion bag and internally of said outer lip, and said capture ring and said outer lip fittingly inserted within said vertically oriented outer wall of said flexible collar and between said bottom wall of said flexible collar and said flexible annular edge.

10. The ultrasound probe of claim 9, wherein said flexible collar has a top wall opposite said bottom wall and said inwardly angled flexible annular edge extends from said top wall.

11. The ultrasound probe of claim 8, wherein said flexible collar when forcedly pressed between two outer points forming a pair of opposite gaps between said flexible annular edge and said substantially cylindrical section.

12. The ultrasound probe of claim 8, wherein said immersion bag has a thickness between 0.1 micron and 250 microns and is made from polyethylene or hydrophilic plastic.

13. The ultrasound probe of claim 8, wherein said flexible collar is preferably made from silicon or other well known flexible materials such as foam, latex, rubber, or plastic.

14. The ultrasound probe of claim 8, wherein said capture ring is made from cardboard, paper or other similar material.

15. The ultrasound probe of claim 8, wherein said outer wall of said flexible collar has a plurality of spaced vertically aligned bars protruding from an outer circumferential surface of said outer wall.

16. The ultrasound probe of claim 8, wherein said flexible collar has a top wall opposite said bottom wall and un upwardly extending protrusion from said top wall, said upwardly extending protrusion indicating an ultrasound transmission direction reference.

17. The ultrasound probe of claim 8, wherein said flexible seal is a self-sealing probe/seal valve.

18. An ultrasound probe comprising an elongated rigid body and an immersion bag, said elongated rigid body having a distal end and a proximal end, said distal end having a substantially cylindrical section, a power/cable attached to and extending externally from said proximal end, an ultrasound transducer attached to said distal end, said immersion bag being made from an acoustically invisible flexible material and containing an ultrasound transmissive material, said immersion bag having an upper open end and a closed lower end and further having an attached flexible collar with an integral annular internal seal for sealing about the upper open end and a tip portion of an ultrasound probe, the integral annular internal seal having at least one self-sealing valve extending along, about and through the annular internal seal thereby providing a unidirectional air passage after the tip portion of the ultrasound probe is in place, thereby providing for the escape of air or liquid from within the immersion bag to limit the pressure therein and close upon partial or complete equalization between the immersion bag interior and ambient pressure.

19. The ultrasound probe of claim 18, wherein said annular flexible sealing edge is a downwardly and inwardly angled extension from said flexible collar.

20. An immersion bag system, for affixation to and use with an ultrasound probe, the system comprising:

a. a flexible immersion bag having an upper open end and a closed lower end and further having an attached flexible collar with an integral annular internal seal for sealing about the upper open end and a tip portion of an ultrasound probe, the integral annular internal seal having at least one self-sealing valve extending along, about and through the annular internal seal thereby providing a unidirectional air passage after the tip portion of the ultrasound probe is in place, thereby providing for the escape of air or liquid from within the immersion bag to limit the pressure therein and close upon partial or complete equalization between the immersion bag interior and ambient pressure;

b. the flexible collar having a curved top wall, the curved top wall having a tapered integral seal extending inwardly and at a downward angle from a curved top wall, the tapered integral seal of the top wall further having an inwardly facing wall annular sealing edge defining a middle opening; and, c. a semi-rigid capture ring having an opening therein.

21. The immersion bag system of claim 20, for affixation to and use with an ultrasound probe, the system wherein the flexible collar has an upwardly extending ultrasound wave reference protrusion.

22. The immersion bag system of claim 20, for affixation to and use with an ultrasound probe, the system wherein the flexible collar has an outer wall having a plurality of vertically aligned bars.

23. The immersion bag system of claim 20, for affixation to and use with an ultrasound probe, the system wherein the ultrasound probe is affixed to the ultrasound probe by frictional engagement of a lower region of the ultrasound probe within the middle opening defined by the inwardly facing wall annular sealing edge of the tapered integral seal.

24. The immersion bag system of claim 23, for affixation to and use with an ultrasound probe, the system wherein the friction engagement provides pressure relieving capability.

25. The immersion bag system of claim 23, for affixation to and use with an ultrasound probe, the system wherein the friction engagement provides maneuvering of the pressure bag system with respect to the lower region of the ultrasound probe.

26. The immersion bag system of claim 20 for affixation to and use with an ultrasound probe, the system wherein the tapered integral seal is fashioned from a flexible, pliable material selected from the group consisting of: silicone, foam, latex, rubber, and plastic.

27. The immersion bag system of claim 26, for affixation to and use with an ultrasound probe, the system wherein the flexible, pliable material is a closed cell foam.

28. The immersion bag system of claim 20, for affixation to and use with an ultrasound probe, the system wherein the semi-rigid capture ring is made of thick walled cardboard.

29. The immersion bag system of claim 20, for affixation to and use with an ultrasound probe, the system wherein the flexible immersion bag is formed of a thin and pliable acoustically invisible material.

30. The immersion bag system of claim 29, for affixation to and use with an ultrasound probe, the system wherein the flexible immersion bag is from about 0.1 microns to about 250 microns thin.

31. The immersion bag system of claim 29, for affixation to and use with an ultrasound probe, the system wherein the flexible immersion bag is formed of polyethylene.

32. The immersion bag system of claim 29, for affixation to and use with an ultrasound probe, the system wherein the flexible immersion bag is formed of hydrophilic plastic.

33. The immersion bag system of claim 29, for affixation to and use with an ultrasound probe, the system wherein the flexible immersion bag has a substantially conical shape.

34. The immersion bag system of claim 29, for affixation to and use with an ultrasound probe, the system wherein the flexible immersion bag has a substantially arcuate end.

35. The immersion bag system of claim 29, for affixation to and use with an ultrasound probe, the system wherein the flexible immersion bag, when assembled in the system, has an outwardly reversed top, the outwardly reversed top forming a lip of annular shape extending about the upper region of the immersion bag for accommodation of the capture ring within the annular shape.

36. The immersion bag system of claim 35, for affixation to and use with an ultrasound probe, the system wherein the flexible collar has a truncated capture annulus and further wherein the lip of the flexible immersion bag and capture ring accommodated within the annular shape of the lip, when assembled in the system, secure within the truncated capture annulus of the flexible collar.

37. The immersion bag system of claim 36, for affixation to and use with an ultrasound probe, the system wherein the truncated capture annulus of the flexible collar includes an outer wall and an inwardly directed horizontal wall, extending a short distance inwardly from the outer wall, which inwardly directed horizontal wall captures the lip of the flexible immersion bag and capture ring accommodated within the annular shape of the lip, within the truncated capture annulus of the flexible collar, so as to maintain the lip and capture ring securely therein.

38. The immersion bag system of claim 37, for affixation to and use with an ultrasound probe, the system wherein the elasticity of the combination of the collar, bag and ring allow assembly of the system and provide a flexible seal against the ultrasound probe to form a probe/seal valve therebetween.

39. The immersion bag system of claim 38, for affixation to and use with an ultrasound probe, the system wherein the probe/seal valve is flexibly movable within the probe/seal valve, such that a transducer at an end of the ultrasound probe is flexibly movable within the immersion bag and sufficiently spaced from the immersion bag to avoid contact during flexible movement.

40. The immersion bag system of claim 39, for affixation to and use with an ultrasound probe, the system wherein the probe/seal valve is self-sealing and manually deformable to allow venting of fluids through the probe/seal valve.

41. The immersion bag system of claim 40, for affixation to and use with an ultrasound probe, the system wherein the probe/seal valve is manually deformable by inwardly exerted force applied to opposing side regions of the outer wall of the flexible collar, which inwardly exerted force temporarily reshapes an assembled system of flexible collar, immersion bag and capture ring about the affixed ultrasound probe, to cause a discontinuous contact of the probe/seal valve at the affixed ultrasound probe, defining a gap, and thereby allowing venting of fluids.

42. The immersion bag system of claim 41, for affixation to and use with an ultrasound probe, the system wherein the manually deformable probe/seal valve is restored to a perfected sealing condition by reducing the forces applied to opposing sides of the outer wall of the flexible collar, thereby eliminating the gap defined by the discontinuous contact due to elastic memory of the assembled system.

* * * * *